United States Patent
Reynolds

(10) Patent No.: US 12,128,068 B2
(45) Date of Patent: *Oct. 29, 2024

(54) COMPOSITIONS AND METHODS FOR DENTAL MINERALIZATION

(71) Applicant: The University of Melbourne, Victoria (AU)

(72) Inventor: Eric Charles Reynolds, Victoria (AU)

(73) Assignee: The University of Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/214,964

(22) Filed: Jun. 27, 2023

(65) Prior Publication Data

US 2024/0033288 A1     Feb. 1, 2024

Related U.S. Application Data

(63) Continuation of application No. 17/832,556, filed on Jun. 3, 2022, now Pat. No. 11,717,537, which is a continuation of application No. 16/852,983, filed on Apr. 20, 2020, now Pat. No. 11,351,193, which is a continuation of application No. 14/906,395, filed as application No. PCT/AU2014/050144 on Jul. 23, 2014, now Pat. No. 10,695,370.

(30) Foreign Application Priority Data

Jul. 23, 2013 (AU) ................. 2013902815

(51) Int. Cl.

| | | |
|---|---|---|
| A61K 33/42 | (2006.01) | |
| A61K 8/21 | (2006.01) | |
| A61K 8/24 | (2006.01) | |
| A61K 8/64 | (2006.01) | |
| A61K 9/68 | (2006.01) | |
| A61K 47/42 | (2017.01) | |
| A61Q 11/00 | (2006.01) | |

(52) U.S. Cl.
CPC ............. *A61K 33/42* (2013.01); *A61K 8/21* (2013.01); *A61K 8/24* (2013.01); *A61K 8/64* (2013.01); *A61K 9/0058* (2013.01); *A61K 47/42* (2013.01); *A61Q 11/00* (2013.01); *A61K 2800/28* (2013.01); *A61K 2800/592* (2013.01)

(58) Field of Classification Search
CPC . A61K 33/42; A61K 8/24; A61K 8/21; A61K 8/64; A61K 9/68; A61K 47/42; A61Q 11/00
USPC ............................................ 424/40, 49, 401
IPC ...................................................... A61Q 11/00
See application file for complete search history.

(56) References Cited

U.S. PATENT DOCUMENTS

| | | |
|---|---|---|
| 3,864,471 A | 2/1975 | King et al. |
| 3,966,901 A | 6/1976 | Cullum et al. |
| 4,080,440 A | 3/1978 | Digiulio et al. |
| 4,157,386 A | 6/1979 | La Rochelle |
| 4,357,318 A | 11/1982 | Shah et al. |
| 4,522,805 A | 6/1985 | Gordon |
| 4,588,763 A | 5/1986 | Brannstrom et al. |
| 4,672,032 A | 6/1987 | Slavkin et al. |
| 5,015,628 A | 5/1991 | Reynolds |
| 5,227,154 A | 7/1993 | Reynolds |
| 5,427,769 A | 6/1995 | Berrocal et al. |
| 5,447,732 A | 9/1995 | Tanimoto et al. |
| 5,520,725 A | 5/1996 | Kato et al. |
| 5,833,953 A | 11/1998 | Berrocal et al. |
| 5,981,475 A | 11/1999 | Reynolds |
| 6,036,944 A | 3/2000 | Winston et al. |
| 6,056,930 A | 5/2000 | Tung |
| 6,120,754 A | 9/2000 | Lee et al. |
| 6,149,894 A | 11/2000 | Yamane et al. |
| 6,214,101 B1 | 4/2001 | Nakaseko |
| 6,652,875 B1 | 11/2003 | Bannister |
| 6,780,844 B1 | 8/2004 | Reynolds |
| 7,312,193 B2 | 12/2007 | Reynolds |
| 7,491,694 B2 | 2/2009 | Reynolds et al. |
| 8,354,117 B2 | 1/2013 | Tsunekawa et al. |
| 8,603,988 B2 | 12/2013 | Reynolds |
| 8,609,071 B2 | 12/2013 | Reynolds |
| 8,673,363 B2 | 3/2014 | Reynolds |
| 9,295,628 B2 | 3/2016 | Reynolds |
| 9,668,945 B2 | 6/2017 | Reynolds |
| 10,695,370 B2 | 6/2020 | Reynolds |
| 10,912,722 B2 | 2/2021 | Reynolds |
| 11,351,193 B2 | 6/2022 | Reynolds |
| 11,504,305 B2 | 11/2022 | Reynolds |

(Continued)

FOREIGN PATENT DOCUMENTS

| | | |
|---|---|---|
| AU | 718253 B2 | 7/1997 |
| CN | 104001157 A | 8/2014 |

(Continued)

OTHER PUBLICATIONS

U.S. Appl. No. 18/052,390, filed Nov. 3, 2022, Reynolds, Eric Charles.
U.S. Appl. No. 18/210,381, filed Jun. 15, 2023, Reynolds, Eric Charles.
U.S. Appl. No. 18/149,989, filed Jan. 4, 2023, Reynolds, Eric Charles.

(Continued)

*Primary Examiner* — Walter E Webb
(74) *Attorney, Agent, or Firm* — Foley & Lardner LLP

(57) ABSTRACT

The present invention relates to compositions for mineralizing a dental surface, in particular tooth enamel. Methods of mineralizing hypomineralized lesions (including subsurface lesions) in the tooth enamel caused by dental caries, dental corrosion and fluorosis are also provided. In particular, the invention relates to a method of mineralizing a dental surface or subsurface comprising contacting the dental surface or subsurface with a compound that is capable of increasing or maintaining the pH of a solution and a mineralizing agent.

17 Claims, No Drawings

(56) References Cited

U.S. PATENT DOCUMENTS

| | | | |
|---|---|---|---|
| 11,564,873 | B2 | 1/2023 | Reynolds |
| 11,717,536 | B2 | 8/2023 | Reynolds |
| 11,717,537 | B2 | 8/2023 | Reynolds |
| 2002/0028251 | A1 | 3/2002 | Okay |
| 2002/0071858 | A1 | 6/2002 | Luo et al. |
| 2003/0124066 | A1 | 7/2003 | Dixon et al. |
| 2003/0152525 | A1 | 8/2003 | Dixon, Jr. et al. |
| 2003/0165442 | A1 | 9/2003 | Baig et al. |
| 2005/0063922 | A1 | 3/2005 | Reynolds et al. |
| 2005/0089481 | A1 | 4/2005 | Yamanaka et al. |
| 2005/0100581 | A1 | 5/2005 | Laurencin et al. |
| 2005/0118115 | A1 | 6/2005 | Fontenot |
| 2006/0183081 | A1 | 8/2006 | Bevilacqua et al. |
| 2007/0071858 | A1 | 3/2007 | Succar et al. |
| 2007/0254260 | A1 | 11/2007 | Alden et al. |
| 2008/0075675 | A1 | 3/2008 | Reynolds |
| 2008/0171001 | A1 | 7/2008 | Engelman et al. |
| 2008/0193557 | A1 | 8/2008 | Reynolds |
| 2009/0016972 | A1 | 1/2009 | Manasherov et al. |
| 2009/0022672 | A1 | 1/2009 | Reynolds |
| 2009/0324662 | A1 | 12/2009 | Kutsch et al. |
| 2010/0028273 | A1 | 2/2010 | Fischer et al. |
| 2011/0076241 | A1 | 3/2011 | Kato et al. |
| 2012/0100194 | A1 | 4/2012 | Yamai et al. |
| 2012/0129135 | A1 | 5/2012 | Yang et al. |
| 2013/0129641 | A1 | 5/2013 | Sadeghpour et al. |
| 2014/0147512 | A1 | 5/2014 | Reynolds |
| 2016/0158283 | A1 | 6/2016 | Reynolds |
| 2017/0333296 | A1 | 11/2017 | Reynolds |
| 2018/0008518 | A1 | 1/2018 | Reynolds |
| 2020/0054672 | A1 | 2/2020 | Reynolds |
| 2020/0197486 | A1 | 6/2020 | Reynolds |
| 2021/0161778 | A1 | 6/2021 | Reynolds |
| 2022/0142881 | A1 | 5/2022 | Reynolds |
| 2022/0183810 | A1 | 6/2022 | Reynolds |
| 2023/0404867 | A1 | 12/2023 | Reynolds |

FOREIGN PATENT DOCUMENTS

| | | | |
|---|---|---|---|
| CN | 1040011574 A | | 8/2014 |
| EA | 011125 B1 | | 12/2008 |
| EP | 0 786 245 A1 | | 7/1997 |
| EP | 1 525 878 B1 | | 3/2007 |
| EP | 1 952 801 A1 | | 8/2008 |
| EP | 2 301 513 A2 | | 3/2011 |
| EP | 2 353 576 A1 | | 8/2011 |
| JP | H08-026925 A | | 1/1996 |
| JP | 08-143436 A | | 6/1996 |
| JP | H08-143436 A | | 6/1996 |
| JP | 10-290682 A | | 11/1998 |
| JP | H11-228327 A | | 8/1999 |
| JP | 11-310599 A | | 11/1999 |
| JP | 3742523 | | 11/1999 |
| JP | H11-310599 A | | 11/1999 |
| JP | 2002-338447 | | 11/2002 |
| JP | 2004-215521 A | | 8/2004 |
| JP | 2005-112841 A | | 4/2005 |
| JP | 2010-047494 A | | 3/2010 |
| JP | 2011-032250 A | | 2/2011 |
| JP | 2013-163656 A | | 8/2013 |
| WO | WO-82/03008 A1 | | 9/1982 |
| WO | WO-87/07615 | | 12/1987 |
| WO | WO-93/03707 | | 3/1993 |
| WO | WO-94/00146 A1 | | 1/1994 |
| WO | WO-96/29340 A1 | | 9/1996 |
| WO | WO-97/36943 A1 | | 10/1997 |
| WO | WO-97/40811 A1 | | 11/1997 |
| WO | WO-98/40406 A1 | | 9/1998 |
| WO | WO-99/471089 | | 9/1999 |
| WO | WO-00/06108 A1 | | 2/2000 |
| WO | WO-00/57842 A1 | | 10/2000 |
| WO | WO-00/57842 A2 | | 10/2000 |
| WO | WO-00/57892 | | 10/2000 |
| WO | WO-01/44106 A1 | | 6/2001 |
| WO | WO-02/094204 A1 | | 11/2002 |
| WO | WO-03/059303 A2 | | 7/2003 |
| WO | WO-03/059304 A1 | | 7/2003 |
| WO | WO-03/099234 | | 12/2003 |
| WO | WO-2004/035077 A1 | | 4/2004 |
| WO | WO-2004/054531 A1 | | 7/2004 |
| WO | WO-2004/060336 A1 | | 7/2004 |
| WO | WO-2006/056013 A1 | | 6/2006 |
| WO | WO-2006/130913 A1 | | 12/2006 |
| WO | WO-2006/135982 A1 | | 12/2006 |
| WO | WO-2007/090242 A1 | | 8/2007 |
| WO | WO-2009/099452 A1 | | 8/2009 |
| WO | WO-2009/130447 A1 | | 10/2009 |
| WO | WO-2010/134904 A1 | | 11/2010 |
| WO | WO-2012/100991 A1 | | 8/2012 |
| WO | WO-2013/117913 A2 | | 8/2013 |
| WO | WO-2014/050144 | | 4/2014 |
| WO | WO-2015/010166 A1 | | 1/2015 |
| WO | WO-2016/101041 A1 | | 6/2016 |
| WO | WO-2018/165707 A1 | | 9/2018 |
| WO | WO-2018/165708 A1 | | 9/2018 |

OTHER PUBLICATIONS

"GC stellt Kasein-haltige Zahnschutzcreme vor—Vorbeugen statt reparieren", DZW Special IDS—Nachlese, 2005, English Abstract, 7 pages.

"MI Paste and MI Paste Plus", [retrieved on Oct. 21, 2014] from http://web.archive.org/web/20131223044114/http://www.gcamerica.com/products/preventive/MI_Paste, published on Dec. 23, 2013 as per Wayback Machine, 2 pages.

"Minimale Intervention fur Maximale Mundgesundheit", DZW Special, 2005, English Abstract, 1 page.

"Minimum Intervention: modernes Kariesmanagement—Weg vom chirurgischen, hin zum medizinischen Versorgungsansatz mit GC", IDS—31st International Dental Show, Cologne, Apr. 12-16, 2005 (Today—Independent Trade Show Daily—Saturday) English Abstract, 2 pages.

"Preventive Agents", The Dental Advisor, vol. No. 21, Issue No. 10, Dec. 2004, pp. 1-6.

"Products for the Dental Hygienist—Desensitizers", The Dental Advisor, vol. No. 23, Issue No. 6, Jul./Aug. 2006, 2 pages.

"Tooth Mousse—Pierre qui roule n'amasse pas mousse? Ben si!", Clinic, vol. No. 27, Apr. 2006, pp. 218-219 (English Abstract).

"Caseine phosphopeptide et phosphate de calcium amorphe: un complexe prometteur", Dialogue Dentaire, Printemps, 2005/W30, pp. 27-29, English Abstract provided.

"Editors' Choice Products—Prospec MI Paste", The Dental Advisor, vol. No. 22, Issue No. 5, Jun. 2005, 1 page.

"GC Tooth Mousse—Eine ganz andere Art der Pravention," Dental Spiegel, Feb. 2005, pp. 53-54.

"Putting mouths where the money is", DPRAsia, Jan./Feb. 2007, pp. 8-10.

"Tradition und modernes know how—ein Erfolgsrezept", Zahn Prax, vol. No. 8, Issue No. 5, 2005, p. 267.

Adamson, N. et al., "The analysis of multiple phosphoseryl-containing casein peptides using capillary zone electrophoresis", J. of Chromatography, vol. No. 646, Jun. 1993, pp. 391-396.

Adamson, N.J. et al., "Characterization of casein phosphopeptides prepared using alcalase: Determination of enzyme specificity", Enzyme and Microbial Tech., vol. No. 19, Aug. 1996, pp. 202-207.

Adamson, N.J. et al., "Characterization of Tryptic Casein Phosphopeptides Prepared Under Industrially Relevant Conditions", Biotec. and Bioeng., vol. No. 45, Issue No. 3, Feb. 1995, pp. 196-204.

Adamson, N.J. et al., "High performance capillary electrophoresis of casein phosphopeptides containing 2-5 phosphoseryl residues: Relationship between absolute electrophoretic mobility and peptide charge and size", Electrophoresis, vol. No. 16, 1995, pp. 525-528.

Adebayo, O.A. et al., "Effects of conditioners on microshear bond strength to enamel after carbamide peroxide bleaching and/or casein phosphopeptide-amorphous calcium phosphate (CPP-ACP) treatment", Journal of Dentistry, vol. No. 35, 2007, pp. 862-870.

Akinmade, A.O. et al., "Review Glass-Ionomer Cements as Adhesives, Part I, Fundamental Aspects and Their Clinical Relevance," Journal of Materials Science: Materials in Medicine, vol. No. 4, 1993, pp. 95-101.

(56) References Cited

OTHER PUBLICATIONS

Al-Zraikat, H. et al., "Development of glass ionomer cement incorporating casein phosphopeptide amorphous calcium phosphate (CPP-ACP) complex", Australian Dental Journal ADRF Special Research Supplement, vol. No. 52, Issue No. 4, 2007, p. S4.

Al-Zraikat, H. et al., "Incorporation of Casein-Phosphopeptide-Amorphous Calcium Phosphate into Glass Ionomer Cement", Abstract 0654, 84th General Session of the IADR, Jun. 28-Jul. 1, 2006, Brisbane, Australia, 1 page.

Allais, G., "Karies—Die Therapie", Journal of Continuing Dental Education, Jun. 2007, pp. 716-735 (German).

Angmar, B. et al., "Studies on the Ultrastructure of Dental Enamel—IV. The Mineralization of Normal Human Enamel", J. Ultrastructure Research, vol. No. 8, 1963, pp. 12-23.

Aoba, T. et al., "Dental Fluorosis: Chemistry and Biology", Crit. Rev Oral Biol. Med., vol. No. 13, Issue No. 2, 2002, pp. 155-170.

Ardu, S. et al., "A minimally invasive treatment of severe dental fluorosis", Quintessence International, vol. No. 38, Issue No. 6, Jun. 2007, pp. 455-458.

Ardu, S. et al., "Minimally invasive treatment of white spot enamel lesions", Quintessence International, vol. No. 38, Issue No. 8, Sep. 2007, pp. 633-636.

Aytepe, Z. et al., "Effect of CCP-ACP on Oral Health of Cerebral Palsy Children", Abstract 3343, Jul. 2008, International Association for Dental Research, Toronto, Canada, 1 page.

Baig, A. et al., "HAP Dissolution Study II: SnF2 vs. NaF Dentifrice Study". 87th Session of the IADR (International & American Associations for Dental Research) Apr. 1-4, 2009 [online], [retrieved on Oct. 21, 2014]. Retrieved from internet, URL: dentalcare.com/media/en-US/research_ db/pdf/, p. 24.

Basting, RT et al., "The Effect of 10% Carbamide Peroxide Bleaching Material on Microhardness of Sound and Demineralized Enamel and Dentin In Situ" {Clinical Research} Operative Dentistry, vol. No. 26, 2001, pp. 531-539.

Bavetta, L.A. et al., "Protein Factors and Experimental Rat Caries", The Journal of Nutrition, vol. No. 63, 1957, pp. 107-117.

Benzian, H. et al., "Total and free available fluoride in toothpastes in Brunei, Cambodia, Laos, the Netherlands and Suriname", International Dental Journal, vol. No. 62, 2012, pp. 213-221.

Biesbrock, A.R. et al., "Reversal of Incipient and Radiographic Caries Through The Use of Sodium and Stannous Fluoride Dentifrices in a Clinical Trial," The Journal of Clinical Dentistry vol. No. IX, Issue No. 1, Feb. 1998, pp. 5-10.

Biesbrock, Aaron R. et al., "Dose response efficacy of sodium fluoride dentifrice at 9 and 21 months with supervised brushing", American Journal of Dentistry, vol. No. 16, Issue No. 5, Oct. 2003, 305-312.

Biesbrock, Aaron R., "Relative anti-caries efficacy of 1100, 1700, 2200, and 2800 ppm fluoride ion in a sodium fluoride dentifrice over 1 year", Community Dentistry and Oral Epidemiology, vol. No. 29, Jan. 2001, pp. 382-389.

Black, G.V. et al., "Mottled Teeth: An Endemic Developmental Imperfection of the Enamel of the Teeth Heretofore Unknown in the Literature of Dentistry", The Dental Cosmos, vol. No. LVIII, Issue No. 2., Feb. 1916, pp. 129-156.

Burwell, A.K. et al. "Dentifrice Protection Against Dentin Demineralization in an In Vitro Study", Abstract 1764, IADR, New Orleans, USA, Mar. 2007, 2 pages.

Burwell, A.K. et al., "Quantitative Tubule Occlusion in an In Vitro Remineralization/Demineralization Model", Abstract 0568, EADR 2006, Dublin, Ireland, Sep. 2006, 3 pages.

Cai, F. et al., "Effect of Addition of Citric Acid and Casein Phosphopeptide-Amorphous Calcium Phosphate to a Sugar-Free Chewing Gum on Enamel Remineralization in Situ", Caries Research, vol. No. 41, Feb. 2007, pp. 377-383.

Cai, F. et al., "Remineralization by Chewing Gum Containing CPP-ACP and Citric Acid", Abstract 190, 84th General Session of the IADR, Brisbane, Australia, Jun. 28, 2006-Jul. 1, 2006, pp. 240-243.

Cai, F. et al., "Remineralization of enamel subsurface lesions in situ by sugar-free lozenges containing casein phosphopeptide-amorphous calcium phosphate", Aus. Dent. J., vol. No. 48, Issue No. 4, 2003, pp. 240-243.

Calcium Glycerophosphate, DrugBank, pp. 1-5, XP002783472 (created Mar. 12, 2015) (retrieved Jul. 31, 2018).

Caplus, "NMR studies of a novel Calcium, phosphate and fluoride delivery vehicle <SYM97> S1-casein(59-79) by stabilized amorphous calcium fluoride phosphate nanocomplexes", Copyright 2005, 4 pages.

Carrillo, J. et al., "Nuevos avances tecnológicos en Odontologia Conservadora", La Gaceta Dental, vol. No. 193, Issue No. 213, Jun. 2008, pp. 218-219 (Spanish).

Chalmers, J. et al., "Minimal Intervention Dentistry in the New Millennium", Dentaltown, Feb. 2008, 2 pages.

Chalmers, J.M., "Minimal intervention dentistry: part 1. Strategies for Addressing the New Caries Challenge in Older Patients", JCDA, vol. No. 72, Issue No. 5, Jun. 2006, pp. 427-433.

Chapple, I.L.C. et al., "Primary prevention of periodontitis: managing gingivitis", Journal of Clinical Periodontology, vol. No. 42, Suppl. 16, 2015, pp. S71-S76.

Chelariu, C. et al., "Nuove prospettive nella prevenzione della carie Congresso Nazionale del Collegio dei Docenti di Odontoiatria Roma", Apr. 5-7, 2006, Poster session, published by "Doctor Os", No. 3, Mar. 2006, English Abstract, 1 page.

Chen, L. et al., "Calcium Release and Mechanical Properties of Experimental Calcium-Releasing Composites", Abstract 2572, IADR, New Orleans, USA, Mar. 2007, 1 page.

Chen, Y. et al., "Research progress of complex of casein phosphopeptide and amorphous calcium phosphate in oral therapy", Chin. J. Aesth. Med., vol. No. 23, Issue No. 8, 2014, pp. 681-683.

CIE Technical Committee, "Colorimetry—Second Edition", Publication CIE No. 15.2, 1986, 85 pages.

Cipolla, M. et al., "Fluoride and Calcium-Phosphate Effects on Fracture Toughness of Bleached Dentin", Abstract 1032, Toronto, Canada, Jul. 2008, 4 pages.

Coates, L., "Tooth mousse shows some unexpected beneficial side effects", Dental Asia, Nov./Dec. 2004, pp. 40-43.

Cochrane, N.J. et al., "QLF and TMR analysis of CPP-ACFP remineralized enamel in vitro", Abstract 192—84th General Session of the IADR, Brisbane, Australia Jun. 28, 2006-Jul. 1, 2006, 1 page.

Colgate, "Fluoride Conversions" colgateprofessional.com, Feb. 2013.

ColgatePalmolive, "Fluoride Conversions" dated Feb. 2013. www.colgateprofessional.com (2013).

Comar, L.P. et al., "Effect of NaF, SnF2, andTiF4 Toothpastes on Bovine Enamel and Dentin Erosion-Abrasion In Vitro", International Journal of Dentistry, vol. No. 2012, Article ID 134350, pp. 1-6.

Crisp, S. et al., "Glass Ionomer Cements: Chemistry of Erosion", J. Dent. Res., vol. No. 55, Issue No. 6, 1976, pp. 1032-1041.

Cross, K.J. et al., "Casein Phosphopeptide-Amorphous Calcium Phosphate Nanocomplexes: A Model of the Casini Micelle Core", Centre for Oral Health Science, School of Dental Science, The University of Melbourne, 2008, pp. 1-42.

Cross, K.J. et al., "Casein Phosphopeptides in Oral Health—Chemistry and Clinical Applications", Current Pharmaceutical Design, vol. No. 13, Issue No. 8, 2007, pp. 793-800.

Cross, K.J. et al., "Cation-dependent structural features of beta-casein-(1-25)", Biochem. J., vol. No. 356, 2001, pp. 277-286.

Cross, K.J. et al., "NMR studies of a novel calcium, phosphate and fluoride delivery vehicle-alphaS1-casein(59-79) stabilized amorphous calcium fluoride phosphate nanocomplexes", Biomaterials, vol. No. 25, 2004, pp. 5061-5069.

Cross, K.J. et al., "Physicochemical Characterization of Casein Phosphopeptide-Amorphous Calcium Phosphate Nanocomplexes", The Journal of Biological Chemistry, vol. No. 280, Issue No. 15, 2005, pp. 15362-15369.

Cross, K.J. et al., "Structural Studies of the b-Casein Phosphopeptide Bound to Amorphous Calcium Phosphate", J. Dent. Res., vol. No. 80, IADR Abstracts, Abstract 0490, 2001, p. 588.

Cross, K.J. et al., "Structure and 15N-Dynamics of Casein Phosphopeptide-Amorphous Calcium Phosphate Nanocomplexes",

(56) References Cited

OTHER PUBLICATIONS

Abstract 2534, 84th General Session of the IADR, Jun. 28-Jul. 1, 2006, Brisbane, Australia, 1 page.

Cross, K.J. et al., "Ultrastructural Studies of the Casein Phosphopeptide-Amorphous Calcium Phosphate Nanoclusters", J. Dent. Res., vol. No. 80, IADR Abstracts, Abstract 0491, 2001, p. 588.

Cross, KJ et al., "Structural characterization of anticariogenic casein phosphopeptide alpha-s2 casein(46-70) complexed with amorphous calcium phosphate", Aust Dent J Adrf Special Research Supplement, vol. No. 52, Issue No. 4, 2007, pp. S10-S11.

Cross, KJ et al., "Structural Characterization of Beta-casein(1-25)-ACFP Complex", Aust Dent J ADRF Special Research Supplement, vol. No. 52, Issue No. 4, 2007, p. S12.

Curnow, M.M.T. et al., "A Randomised Controlled Trial of the Efficacy of Supervised Toothbrushing in High-Caries-Risk Children", Caries Research, vol. No. 36, 2002, pp. 294-300.

Database WPI Week 200316, Thomason Scientific, London, GB, 2003-165149, XP002537968 & SE 0 100 558 A, Mediteam Dental AB, Aug. 21, 2002, Abstract, 2 pages.

Davies, G.M. et al., "A randomized controlled trial of the effectiveness of providing free fluoride toothpaste from the age of 12 months on reducing caries in 5-6 year old children", Community Dental Health, vol. No. 19, 2002, pp. 131-136.

De Oliveira, A. et al., "In situ effect of a CPP-ACP chewing gum on enamel erosion associated or not with abrasion", Clin Oral Investig, vol. No. 21, Mar. 2016, pp. 339-346.

Deangelis, A.F. et al., "Molecular modelling of anticariogenic casein phosphopeptide aS2-CN(2-20) NMR spectroscopy derived constraints", Abstract 2997, 82nd General Session of the IADR, Mar. 2004, Honolulu, Hawaii, 1 page.

Denbesten, P.K. et al., "Biological Mechanisms of Fluorosis and Level and Timing of Systemic Exposure to Fluoride with Respect to Fluorosis", J Dent Res, vol. No. 71, Issue No. 5, May 1992, pp. 1238-1243.

Denes, G. et al., "Oxidation of SnF2 stannous fluoride in aqueous solutions", Hyperfine Interactions, vol. No. 90, 1994, pp. 435-439.

Donovan, T., "Protocol for the prevention and management of root caries", Journal Compilation, vol. No. 20, Issue No. 6, 2008, pp. 405-411.

Duckworth, R.M. et al., "Effects of Mouthwashes of Variable NaF Concentration but Constant NaF Content on Oral Fluoride Retention", Caries Research, vol. No. 28, 1994, pp. 43-47.

Duckworth, R.M. et al., "Oral Fluoride Measurements for Estimation of the Anti-caries Efficacy of Fluoride Treatments", J Dent Res, vol. No. 71, Spec Iss, Apr. 1992, pp. 836-840.

Fahad, A.H. et al., "Effect of casein phosphopeptide-amorphous calcium phosphate on the microhardness and microscopic features of the sound enamel and initial caries-like lesion of permanent teeth, compared to fluoridated agents," Journal of Baghdad College Dentistry, vol. No. 24, Issue No. 4, 2012, pp. 114-120.

Farooq, I. et al., "A review of novel dental caries preventative material: Casein phosphopeptide-amorphous calcium phosphate (CPP-ACP) complex," King Saud University Journal of Dental Sciences, vol. No. 4, 2013, pp. 47-51.

Featherstone, J.D.B. et al., "An in situ Model for Simultaneous Assessment of Inhibition of Demineralization and Enhancement of Remineralization", J Dent Res, vol. No. 71, Spec. Iss., Apr. 1992, pp. 804-810.

Feinmann, J., "This won't hurt a bit," The Times, body&soul news, Mar. 12, 2005, pp. 4-5.

Fejerskov, O. et al, "The Effect of Fluoride on Tooth Mineralization", Fluoride in Dentistry—2nd edition, Chapter 8, Munksgaard, Copenhagen, 1996, pp. 112-152.

Fejerskov, O. et al., "Dental fluorosis—a handbook for health workers", Munksgaard, Copenhagen, 1988, pp. 32-77.

Fejerskov, O. et al., "Posteruptive changes in human dental fluorosis—a histological and ultrastructural study", Proc Finn Dent Soc, vol. No. 87, Issue No. 4, 1991, pp. 607-619.

Fejerskov, O. et al., "The Nature and Mechanisms of Dental Fluorosis in Man", J Dent Res, vol. No. 69, Spec Iss, Feb. 1990, pp. 692-700.

Ferrazzano, G.F. et al., "New Strategies in dental caries prevention: experimental study on casein phosphopetides", European Journal of Paedetric Dentistry, vol. No. 4, 2007, pp. 183-187.

Ferrazzano, G.F. et al., "Nuove strategie nella prevenzione della carie dentaria:studio sperimentale sui caseinofosfopeptidi", Prevenzione Odontostomatologica, vol. No. 4, 2005, pp. 15-21 SPANISH.

Ferrazzano, G.F. et al., "Protective effect of yogurt extract on dental enamel demineralization in vitro", Australian Dental Journal, vol. No. 53, 2008, pp. 314-319.

Freml, L. et al., "Efficacy of Hypersensitivity Agents on Demineralization under Provisional Crowns", Abstract 1346, IADR Mar. 2007, New Orleans, USA, 2 pages.

Fuller, B.L. et al., "Efficacy of MI Paste in Preventing Demineralization in Overdenture Abutments", Abstract 0503, IADR Mar. 2007, New Orleans, USA, 2 pages.

Gagnaire, V. et al., "Phosphopeptides interacting with colloidal calcium phosphate isolated by tryptic hydrolysis of bovine casein micelles", Journal of Dairy Research, vol. No. 63, 1996, pp. 405-422.

Gandolfi, M.G. et al., "Calcium silicate coating derived from Portland cement as treatment for hypersensitive dentine", Journal of Dentistry, vol. No. 36, 2008, pp. 565-578.

GC America, Inc. "MI Paste™ and MI Paste Plus ™ with Recaldent™ (CPP-ACP)", Inside Dentistry, vol. No 8, Issue No. 10, Oct. 2012 [online], [retrieved on Oct. 21, 2014]. Retrieved from internet, URL: www .dentalaegis.com/id/201 21 1 O/mi-paste-and-mi-paste-p 1 us-with-recaldent-cpp-acp>, 6 pages.

Giambro, N.J. et al., "Characterization of Fluorosed Human Enamel by Color Reflectance, Ultrastructure, and Elemental Composition", Caries Res., vol. No. 29, 1995, pp. 251-257.

Giniger, M. et al., "A 180-Day Clinical Investigation of the Tooth Whitening Efficacy of a Bleaching Gel with Added Amorphous Calcium Phosphate", J. of Clinical Dentistry. Vol. No. 16, Issue No. 1, 2005, pp. 11-16.

Giniger, M. et al., "The clinical performance of professionally dispensed bleaching gel with added amorphous calcium phosphate", JADA, vol. No. 136, Mar. 2005, pp. 383-392.

Gisselsson, H., et al., "Effect of professional flossing with NaF or SnF2 gel on approximal caries in 13-16-year-old schoolchildren", Acta Odontologica Scandinavica, vol. No. 57, Issue No. 2, 1999, pp. 121-125.

Gugnani, S. et al., "Comparative evaluation of two commercially available desensitizing agents after scaling and root planing: an in vivo study", PERIO, vol. No. 5, Issue No. 2, 2008, pp. 121-129.

Haderlie, D.C. et al., "MI Paste and Fluoride effects on Secondary Caries", Abstract 0504, IADR Mar. 2007, New Orleans, USA, 2 pages.

Harper, D.S. et al., "Cariostatic Evaluation of Cheeses with Diverse Physical and Compositional Characteristics", Caries Res., vol. No. 20, 1986, pp. 123-130.

Harper, D.S. et al., "Modification of Food Cariogenicity in Rats by Mineral-Rich Concentrates from Milk", J. Dent Res., vol. No. 66, Issue No. 1, Jan. 1987, pp. 42-45.

Hartshorne, JE et al., "The relationship between plaque index scores, fluoride content of plaque, plaque pH, dental caries experience and fluoride concentration in drinking water in a group of primary school children", Journal of the Dental Association of South Africa, vol. No. 49, Jan. 1994, pp. 5-10.

Hay, K.D. et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod., vol. No. 93, Issue No. 3, Mar. 2002, pp. 271-275.

Haywood, V.B. et al., "History, safety, and effectiveness of current bleaching techniques and applications of the nightguard vital bleaching technique", Quintessence Int., vol. No. 23, Issue No. 7, Jul. 1992, pp. 471-488.

Hicks, J. et al., "Biological factors in dental caries: role of remineralization and fluoride in the dynamic process of demineralization and

(56) References Cited

OTHER PUBLICATIONS remineralization (part 3)", The Journal of Clinical Pediatric Dentistry, vol. No. 28, Issue No. 3, 2004, pp. 203-214.
Hicks, J. et al., "Casein Phosphopeptide-Amorphous Calcium Phosphate Paste: Root Surface Caries Formation", Abstract 3275, IADR, Baltimore, Maryland, Mar. 2005, 1 page.
Hidaka, S. et al., "A New Method for Study of the Formation and Transformation of Calcium Phosphate Precipitates: Effects of Several Chemical Agents and Chinese Folk Medicines", Archives of Oral Biol., vol. No. 36, Issue No. 1, 1991, pp. 49-54.
Holler, B.E. et al., "Fluoride uptake and distribution in enamel and dentin after application of different fluoride solutions", Clin Oral Invest, vol. No. 6, 2002, pp. 137-144.
Holloway, P.J. et al., "Effects of Various Sucrose: Casein Ratios in Purified Diets on the Teeth and Supporting Structures of Rats", Arch. Oral Biol., vol. No. 3, 1961, pp. 185-200.
Holt, C. et al., "Ability of a b-casein phosphopeptide to modulate the precipitation of calcium phosphate by forming amorphous dicalcium phosphate nanoclusters", Biochem J., vol. No. 314, 1996, pp. 1035-1039.
Holt, C., "An equilibrium thermodynamic model of the sequestration of calcium phosphate by casein micelles and its application to the calculation of the partition of salts in milk", European Biophysics Journal, 2004, pp. 421-434.
Huang, A. et al., "Remineralization of Eroded Teeth Using CPP-ACP Paste", Abstract 3267, International Association for Dental Research, Toronto, Canada, Jul. 2008, 1 page.
Huq, N.L. et al., "Nascent Helix in the Multiphosphorylated Peptide as2—Casein(2-20)", Journal of Peptide Science, vol. No. 9, 2003, pp. 386-392.
Huq, N.L. et al., "A 1H-NMR study of the casein phosphopeptide as1-casein (59-79)", Biochimica et Biophysica Acta, vol. No. 1247, 1995, pp. 201-208.
Huq, N.L. et al., "Molecular Modeling of a Multiphosphorylated Sequence Motif Bound to Hydroxyapatite Surfaces", J. Mol. Model., vol. No. 6, 2000, pp. 35-47.
Huq, N.L. et al., "Molecular modelling of the multiphosphorylated casein phosphopeptide aS1-casein(59-79) based on NMR constraints", J. Dairy Res., vol. No. 71, 2004, pp. 28-32.
Iijima, Y. et al., "Acid Resistance of Enamel Subsurface Lesions Remineralized by a Sugar-Free Chewing Gum Containing Casein Phosphopeptide-Amorphous Calcium Phosphate", Caries Res., vol. No. 38, 2004, pp. 551-556.
Iijima, Y. et al., "Acid Resistance of Remineralized Enamel by a Sugar-Free Chewing Gum", Abstract 0184, 84th General Session of the IADR, Jun. 28-Jul. 1, 2006, Brisbane, Australia, 1 page.
Imfeld, T., "Prevention of progression of dental erosion by professional and individual prophylactic measures," Eur J Oral Sci, vol. No. 104, 1996, pp. 215-220.
Inaba, D. et al. "Intraoral changes in NaOCl-treated Root Dentin Lesions: A Pilot Study.", J. Dental Health, vol. No. 50, 2000, pp. 824-826, Abstract.
Inaba, D. et al., "Effect of Sodium Hypochlorite Treatment on Remineralization of Human Root Dentine in vitro", Caries Research, vol. No. 30, 1996, pp. 218-224.
Kandelman, D. et al., "A 24-month Clinical Study of the Incidence and Progression of Dental Caries in Relation to Consumption of Chewing Gum Containing Xylitol in School Preventive Programs", J Dent Res, vol. No. 69, Issue No. 11, Nov. 1990, pp. 1771-1775.
Kariya, S. et al., "Fluoride Effect on Acid Resistance Capacity of CPP-ACP Containing Material", Abstract 2045, 82nd General Session of the IADR, Mar. 2004, Honolulu, Hawaii, 1 page.
Kariya, S. et al., "Remineralization of Enamel Lesion by a Novel Cream with both CPP-ACP and Fluoride", Poster Session 136, 54th Annual ORCA Congress, 2007, 1 page.
Keçik, D. et al., "Effect of Acidulated Phosphate Fluoride and Casein Phosphopeptide-Amorphous Calcium Phosphate Application on Shear Bond Strength of Orthodontic Brackets", Angle Orthodontist, vol. No. 78, Issue No. 1, 2008, pp. 129-133.

Khan, S., "White Spots on Teeth", Buzzle.com, https://www.buzzle.com/articles/white-spots-on-teeth.html, published Jan. 8, 2010, 2 pages.
Kilian, M. et al., "The oral microbiome—an update for oral healthcare professionals", British Dental Journal, vol. No. 221, Issue No. 10, Nov. 18, 2016, pp. 657-666.
Kim, K.-B. et al., "Remineralization of the artificial caries lesion using CPP-ACP and fluoride", Abstract 3280, International Association for Dental Research, Toronto, Canada, Jul. 2008, 1 page.
Kowalczyk, A. et al., "Evaluation of the product based on Recaldent™ technology in the treatment of dentin hypersensitivity", Advances in Medical Sciences, vol. No. 51, Suppl. 1, 2006, pp. 40-42.
Krobicka, A. et al., "The Effects of Cheese Snacks on Caries in Desalivated Rats", J. Dent Res., vol. No. 66, Issue No. 6, Jun. 1987, pp. 1116-1119.
Kumar, VLN et al., "The effect of casein phosphopeptide-amorphous calcium phosphate on remineralization of artificial caries-like lesions: an in vitro study", Australian Dental Journal, vol. No. 53, 2008, pp. 34-40.
Lasfargues, J. et al., "La Remineralisation Des Lesions Carieuses (2) Synergies Therapautiques", Realites Cliniques, vol. No. 15, Issue No. 3, 2004, pp. 261-275, English Abstract.
Legeros, R.Z., "Calcium Phosphates in Demineralization/Remineralization Processes", J Clinical Dent, vol. No. 10, Issue No. 2, 1999, pp. 65-73.
Lewis, J., "Brush, floss and mousse?", Women Dentistry Journal, Winter 2005, vol. No. 2, Issue No. 4, pp. 18-19.
Little, E. et al., "An equilibrium thermodynamic model of the sequestration of calcium phosphate by casein phosphopeptides", European Biophysics Journal, vol. No. 33, 2004, pp. 435-447.
Llena, C. et al., "Anticariogenicity of Casein Phosphopeptide-amorphous Calcium Phosphate: A Review of the Literature", The Journal of Contemporary Dental Practice, vol. No. 10, Issue No. 3, May 2009, pp. 1-9.
Loesche, W.J., "Role of *Streptococcus mutans* in Human Dental Decay", Microbial. Rev., vol. No. 50, Issue No. 4, Dec. 1986, pp. 353-380.
Lynch, R.J.M. et al, "Low-Levels of fluoride in plaque and saliva and their effects on the demineralisation and remineralisation of enamel; role of fluoride toothpastes", International Dental Journal, vol. No. 54, Issue No. 5, pp. 304-309.
Madhavan, S. et al., "Dentinal hypersensitivity: A comparative clinical evaluation of CPP-ACPF, sodium fluoride, propolis, and placebo", Journal of Conservative Dentistry, 2012; 15(4): 315-318.
Malcmacher, L., "Enamel Remineralization: The Medical Model of Practicing Dentistry", Dentistry Today, Nov. 2006, 2 pages.
Malcmacher, L., "Vitamins for teeth", Common Sense Dentistry, www.dentaleconomics.com, Oct. 2006, pp. 130 and 144.
Manton, D.J. "Dental Caries: Where to From Here?", Ann Roy Australas Coll Dent Surg, vol. No. 19, 2008, pp. 73-76.
Manton, D.J. et al., "In Situ Remineralisation by Sugar-Free Gums, One Containing CPP-ACP", Abstract 0020, 45th Annual Meeting of Australian/New Zealand Division of the IADR, Sep. 2005, 1 page.
Manton, D.J. et al., "Remineralization of enamel subsurface lesions in situ by the use of three commercially available sugar-free gums", International Journal of Paediatric Dentistry, vol. No. 18, 2008, pp. 284-290.
Manton, D.J. et al., "Remineralization of White Spot Lesions in situ by Tooth Mousse", Abstract 0185, 84th General Session of the IADR, Jun. 28-Jul. 1, 2006, Brisbane, Australia, 1 page.
Manton, D.J., "Promoting Remineralization: Using Casein Phosphopeptide-Stabilized Amorphous Calcium (Fluoride) Phosphate. A Chemical Approach", EAPD, Amsterdam, Jun. 8-11, 2006, 1 page.
Manton, DJ et al., "Effect of ozone and Tooth Mousse™ on the efficacy of peroxide bleaching", Australian Dental Journal, vol. No. 53, 2008, pp. 128-132.
Martinez-Pablon, M. et al., "Comparison of the Effect of Two Sugar-Substituted Chewing Gums on Different Caries- and Gingivitis-Related Variables: A Double-Blind, Randomized, Controlled Clinical Trial", Clinical Oral Investigations, vol. No. 18, 2014, pp. 589-598.

(56) References Cited

OTHER PUBLICATIONS

Mazzaoui, S.A. et al., "Incorporation of Casein Phosphopeptide-Amorphous Calcium Phosphate into a Glass-ionomer Cement", Journal of Dental Research, vol. No. 82, Issue No. 11, 2003, pp. 914-918.

Melkers, M.J., "Keeping Focused on the Finish Line . . . Accomplishing Goals with Traditional and Progressive Technologies", Dentaltown, vol. No. 5, Issue No. 11, Nov. 2004, pp. 60, 62, 64 & 66.

Mellberg, J.R. et al., "Effect of soluble calcium on fluoride uptake by enamel from sodium monofluorophosphate", J Dent Res., vol. No. 61, Issue No. 12, Dec. 1982, pp. 1394-1396.

MI Paste ™ and MI Paste Plus™ [retrieved on Feb. 16, 2015] Retrieved from internet , URL: http://web.archive.org/web/20140701070616/http://www.mipaste.com/about.php> published on Dec. 4, 2013 as per Wayback Machine whole document Wayback machine used to determine publication date, 2 pages.

Mickenautsch, S., "An Introduction to Minimal Intervention Dentistry (MI)", Dental News, vol. No. XIV, Issue No. IV, 2007, pp. 13-20.

Milnar, F.J., "Considering Biomodification and Remineralization Techniques as Adjuncts to Vital Tooth-Bleaching Regimens", Compendium, vol. No. 28, Issue No. 5, May 2007, pp. 234-240.

Min, S. et al., "Progress in the treatment of dentin hypersensitivity", Anhui Medical and Pharmaceutical Journal, vol. No. 16, Issue No. 10, Oct. 2012, pp. 1521-1523.

Minami, K. et al., "Effects of Cheese and Milk Containing CPP-ACP on Enamel Remineralization", 2049—82nd General Session of the IADR, Mar. 2004, Honolulu, Hawaii, 1 page.

Mintel, "Mineralising Toothpaste," from Database GNPD, Database Accession No. 1368327, Aug. 2010, 3 pages.

Misra, S. et al., "Early Childhood Caries—A Review", Dental Update, vol. No. 34, Dec. 2007, pp. 556-564.

Mitthra, S. et al., "Mineral Loss before and after Bleaching and Mineral Uptake on Application of Remineralizing Agent", Indian Journal of Multidisciplinary Dentistry and Endodontics, vol. No 1, Issue No. 1, Jan. 2010, 4 pages.

Miyazaki, M. et al., "Using Ultrasound Transmission Velocity to Analyze Demineralization of Tooth Substrate", Abstract 94, 52nd ORCA Congress, Jul. 2005, Indianapolis, USA, Caries Res, vol. No. 39, p. 319.

Morgan, M.V. et al. "A Clinical Trial Measuring White Spot Lesion Progression and Regression", Abstract 0112, Jul. 2008, Toronto, Canada, 1 page.

Morgan, M.V. et al., "CPP-ACP gum slows progression and enhances regression of dental caries", Abstract 2445, 84th General Session of the IADR, Jun. 28-Jul. 1, 2006, Brisbane, Australia, 1 page.

Morgan, M.V. et al., "The Anticariogenic Effect of Sugar-Free Gum Containing CPP-ACP Nanocomplexes on Approximal Caries Determined Using Digital Bitewing Radiography", Caries Research, vol. No. 42, 2008, pp. 171-184.

Morgan, MV et al., "Clinical Trial of Tooth Mousse on White Spot Lesions", Cooperative Research Centre for Oral Health Science, Briefing Paper No. 2, Jul. 2008, 4 pages.

Moule, C.A. et al., "Resin bonding using an all-etch or self-etch adhesive to enamel after carbamide peroxide and/or CPP-ACP treatment", Australian Dental Journal, vol. No. 52, Issue No. 2, 2007, pp. 133-137.

Mount, GJ, "A new paradigm for operative dentistry", Australian Dental Journal, vol. No. 52, Issue No. 4, 2007, pp. 264-270.

Munjal, D. et al., "Assessment of White Spot Lesions and In-Vivo Evaluation of the Effect of CPP-ACP on White Spot Lesions in Permanent Molars of Children", Journal of Clinical and Diagnostic Research, vol. No. 10, Issue No. 5, May 2016, pp. 149-154.

Murata, Y. et al., "Remineralization Power by Xylitol Chewing Gums", Abstract 2046, 82nd General Session of the IADR, 2004, Honolulu, Hawaii, 1 page.

Narayana, T. et al., "An in vitro study of wear prevention in dentine", Abstract 2424, 84th General Session of the IADR, Jun. 28-Jul. 1, 2006, Brisbane, Australia, 1 page.

Ng, F. et al., "Aesthetic management of severely fluorosed incisors in an adolescent female", Australian Dental Journal, vol. No. 52, Issue No. 3, 2007, pp. 243-248.

O'Hehir, T., "Caries—More Than a Filling", Hygientown.com, Jul./Aug. 2008, pp. 8-12.

Ono, T. et al., "Complexes of Casein Phosphopeptide and Calcium Phosphate Prepared from Casein Micelles by Tryptic Digestion", Biosci. Biotech. Biochem., vol. No. 58, Issue No. 8, 1994, pp. 1376-1380.

Ono, T. et al., "Preparation of Casein Phosphopeptides from Casein Micelles by Ultrafiltration", Biosci. Biotech. Biochem., vol. No. 59, Issue No. 3, 1995, pp. 510-511.

Oshiro, M. et al., "Effect of CPP-ACP paste on tooth mineralization: an FE-SEM study", Journal of Oral Science, vol. No. 49, Issue No. 2, 2007, pp. 115-120.

P.J. Eke, et al. "Prevalence of Periodontitis in Adults in the United States: 2009 and 2010." J Dent Res 91:914-920 (2012). (Year: 2012).

Pelletier, P. et al., "Study of the Hyrolyisis Reaction of the P03F2 Anion in Aqueous Solution", Z. Anorg. Alig. Chem., 1990, vol. No. 581, pp. 190-198.

Perdigao, J. et al., "Contemporary Trends and Techniques in Tooth Whitening: A Review", Practical Procedures & Aesthetic Dentistry, vol. No. 16, Issue No. 3, 2004, pp. 185-192.

Perich, J.W. et al., "Efficient Solution-Phase Synthesis of Multiple O-Phosphoseryl-Containing Peptides Related to Casein and Statherin", Int. J. Pept. Protein Res., vol. No. 40, 1992, pp. 81-88.

Perich, J.W. et al., "The Use of Synthetic Phosphopeptides for Epitope Mapping of the aS1-Casein Phosphopeptide Segment 59-70", Bioorg. Med. Chem. Lett., vol. No. 2, 1992, pp. 1153-1154.

Peschke, J.C. et al., "Nucleating Ability of Calcium Phosphate-Protein-Composites", Abstract 2244, IADR, Mar. 2007, New Orleans, USA, 2 pages.

Piekarz, C. et al., "An in vitro assessment of the role of Tooth Mousse in preventing wine erosion", Australian Dental Journal, vol. No. 53, 2008, pp. 22-25.

Pietrzycka, K. et al., "Chemical methods of treatment of dental caries: the action and application of CPP-ACP", Kwartalnik Stomatologa Praktyka Polish & English Journal for Dentists, E-Dentico, vol. No. 2, Issue No. 18, 2008, pp. 68-74.

Pitts, N.B., "Are We Ready to Move from Operative to Non-Operative/Preventive Treatment of Dental Caries in Clinical Practice? ", Caries Res, vol. No. 38, 2004, pp. 294-304.

Plate, U. et al., "Investigation of the early mineralisation on collagen in dentine of rat incisors by quantitative electron spectroscopic diffraction (ESD)", Cell Tissue Res, vol. No. 278, 1994, pp. 543-547.

Poitevin, A. et al., "Clinical Effectiveness of a CPP-ACP Creme for Tooth Hypersensitivity Treatment", EADR Istanbul, Aug. 24-28, 2004, Abstract 0136, 1 page.

Quartarone, E. et al., "Surface kinetic roughening caused by dental erosion: an atomic force microscopy study", Journal of Applied Physics, vol. No. 103, 2008, 104702, 6 pages.

Rahiotis, C. et al., "Characterization of oral films formed in the presence of a CPP-ACP agent: An in situ study", Journal of Dentistry, vol. No. 36, 2008, pp. 272-280.

Rahiotis, C. et al., "Effect of a CPP-ACP agent on the demineralization and remineralization of dentine in vitro", Journal of Dentistry, vol. No. 35, 2007, pp. 695-698.

Ramadas, Y., "The oral care for children with malignancies", Synopses: The Newsletter of the Australian and New Zealand Society of Paediatric Dentistry, Issue No. 28, Mar. 2004, pp. 1-20.

Ramalingam, L. et al., "Adding Caesin Phosphopetide-amorphous Calcium Phosphate to Sports Drinks to Eliminate In Vitro Erosion", Pediatric Dentistry, vol. No. 27, Issue No. 1, 2005, pp. 61-67.

Ramalingam, L. et al., "An in Vitro Investigation of the Effects of Casein Phosphopeptide-Stabilized Amorphous Calcium Phosphate (CPP-ACP) on Erosion of Human Dental Enamel by a Sports Drink", J Dent Res., vol. No. 81, Spec Iss A, 2002, Abstract 2810, p. A-351.

Ramalingam, L. et al., "Erosion of Human Dental Enamel by Sports Drinks", Synopses, vol. No. 27, 2003, pp. 16-19.

(56) References Cited

OTHER PUBLICATIONS

Ranjitkar, S. et al., "Enamel wear prevention under conditions simulating bruxism and acid regurgitation", Abstract 2428, 84th General Session of the IADR, Jun. 28-Jul. 1, 2006, Brisbane, Australia, 1 page.

Ranjitkar, S. et al., "The Role of Tooth Mousse in preventing enamel wear," Poster 0375, Session 39, 42nd Annual Meeting of IADR, Continental European and Israeli Divisions, Sep. 26-29, 2007, 1 page.

Ranjitkar, S. et al., "The Role of Tooth Mousse in Reducing Erosive Tooth Wear", Abstract 2500, International Association for Dental Research, Jul. 2008, Toronto, Canada, 1 page.

Rees, J. et al., "Pronamel and tooth mousse: An initial assessment of erosion prevention in vitro", Journal of Dentistry, vol. No. 35, 2007, pp. 355-357.

Reeves, R. et al., "Calcium Phosphate Sequestering Phosphopeptide from Casein", Science, vol. No. 128, 1958, p. 472.

Reich, E., "Das kleine gewisse Etwas zur Remineralisation", Zahnmedizin, vol. No. 95, Issue No. 21, 2005, pp. 2-9, English Abstract.

Reich, E., "Die Betreuung von Kariespatienten in der Praxis", Quintessenz, vol. No. 59, Issue No. 12, 2008, pp. 1301-1307, English Abstract.

Reich, E., "Flüssiger Zahnschmelz", Dental Magazine, 2005, English Abstract, 4 pages.

Reich, E., "GC Tooth Mousse—Ein neuer Ansatz zur Remineralisation", Kongress: Wissenschaft und Praxis der Sanften Zahnheilkunde, Lindau am Bodensee, Mar. 3-4, 2006, English Abstract, 4 pages.

Reich, E., Dental Products Report Europe, Jan. 1, 2006, 9 pages.

Retention in Plaque and Remineralization of Enamel Lesions by Various Forms of Calcium in a Mouthrinse or Sugar-Free Chewing Gum, School of Dental Science, The University of Melbourne pp. 1-24.

Reynolds, E., "The Role of Phosphopeptides in Caries Prevention", Dental Perspectives, Edition 3, Nov. 1999, pp. 6-7.

Reynolds, E.C. et al., "Confectionary Composition and Rat Caries", Caries Res., vol. No. 21, 1987, pp. 538-545.

Reynolds, E.C. et al., "Effect of Adsorbed Protein on Hydroxyapatite Zeta Potential and Streptococcus mutans Adherence", Infection and Immunity, vol. No. 39, Issue No. 3, Mar. 1983, pp. 1285-1290.

Reynolds, E.C. et al., "Effect of Casein and Whey-Protein Solutions on Caries Experience and Feeding Patterns of the Rat", Archs. oral. Biol., vol. No. 29, Issue No. 11, 1984, pp. 927-933.

Reynolds, E.C. et al., "Enamel Remineralization by Chewing Gum Containing Casein Phosphopeptide-Amorphous Calcium Phosphate", J Dent Res, vol. No. 80, IADR Abstracts, Abstract 0489, 2001, p. 588.

Reynolds, E.C. et al., "Phosphoprotein Inhibition of Hydroxyapatite Dissolution", Calcif. Tissue Int., vol. No. 34, 1982, pp. S52-S56.

Reynolds, E.C. et al., "Protein Dissimilation by Human Salivary-sediment Bacteria", J. Dent.Res., vol. No. 68, Issue No. 1, Feb. 1989, pp. 124-129.

Reynolds, E.C. et al., "Reduction of Chocolate's Cariogenicity by Supplementation with Sodium Caseinate", Caries Res., vol. No. 21, 1987, pp. 445-451.

Reynolds, E.C. et al., "Retention in Plaque and Remineralization of Enamel Lesions by Various Forms of Calcium in a Mouthrinse or Sugar-free Chewing Gum", J Dent Res, vol. No. 82, Issue No. 3, 2003, pp. 206-211.

Reynolds, E.C. et al., "A Review of the Effect of Milk on Dental Caries", Aust. J. Dairy Tech., vol. No. 34, Dec. 1979, pp. 175-179.

Reynolds, E.C. et al., "A Selective Precipitation Purification Procedure for Multiple Phosphoseryl-Containing Peptides and Methods for Their Identification", Anal. Biochem., vol. No. 217, Issue No. 2, 1994, pp. 277-284.

Reynolds, E.C. et al., "Additional Aids to the Remineralisation of Tooth Structure," Preservation and Restoration of Tooth Structure, Chapter 8, 2005, pp. 111-118.

Reynolds, E.C. et al., "Advances in Enamel Remineralization: Casein Phosphopeptide-Amorphous Calcium Phosphate", J. Clin. Dent., vol. No. X, Issue No. 2, 1999, pp. 86-88.

Reynolds, E.C. et al., "Anticariogenicity of Calcium Phosphate Complexes of Tryptic Casein Phosphopeptides in the Rat", J Dent Res, vol. No. 74, Issue No. 6, 1995, pp. 1272-1279.

Reynolds, E.C. et al., "Cariogenicity of a Confection Supplemented with Sodium Caseinate at a Palatable Level", Caries. Res., vol. No. 23., 1989, pp. 368-370.

Reynolds, E.C. et al., "Effect of Milk on Caries Incidence and Bacterial Composition of Dental Plaque in the Rat", Archs oral Biol., vol. No. 26, Issue No. 5, 1981, pp. 445-451.

Reynolds, E.C. et al., "Fluoride and Casein Phosphopeptide-Amorphous Calcium Phosphate", J Dent Res, vol. No. 87, Issue No. 4, 2008, pp. 344-348.

Reynolds, E.C. et al., "Improved Plaque Uptake and Enamel Remineralization by Fluoride with CPP-ACP", Abstract 2538, 84th General Session of the IADR, Jun. 28-Jul. 1, 2006, Brisbane, Australia, 1 page.

Reynolds, E.C., "The Prevention of Sub-surface Demineralization of Bovine Enamel and Change in Plaque Composition by Casein in an Intra-oral model", J. Dental Res., vol. No. 66, Issue No. 6, 1987, pp. 1120-1127.

Reynolds, E.C., "Anticariogenic Casein Phosphopeptides", Prot. Peptide Lett., vol. No. 6, Issue No. 5, 1999, pp. 295-303.

Reynolds, E.C., "Anticariogenic complexes of amorphous calcium phosphate stabilized by casein phosphopeptides: A review", Journal of Special Care in Dentistry, vol. No. 18, Issue No. 1, Jan./Feb. 1998, pp. 8-16.

Reynolds, E.C., "Calcium phosphate-based remineralizatron systems: scientific evidence?", Australian Dental Journal, vol. No. 53, 2008, pp. 268-273.

Reynolds, E.C., "Caries Prevention and Oral Health", Health Aspects of Dairy Products/Caries Prevention and Oral Health, 2002, pp. 1306-1313.

Reynolds, E.C., "Dairy Components in Oral Health", Aust. J. Dairy Tech., vol. No. 58, Issue No. 2, Aug. 2003, pp. 79-81.

Reynolds, E.C., "Dairy Products and Dental Health," Proceedings of the Nutrition Society of Australia, 1995, pp. 95-102.

Reynolds, E.C., "Remineralization of Enamel Subsurface Lesions by Casein Phosphopeptide-stabilized Calcium Phosphate Solutions", J Dent Res., vol. No. 76, Issue No. 9, Sep. 1997, pp. 1587-1595.

Reynolds, EC., "Remineralization of early enamel caries by anticariogenic casein phosphopeptide-amorphous calcium phosphate nanocomplexes", Dental Practice, Nov./Dec. 2001, 3 pages.

Roberts, A.J., "Role of Models in Assessing New Agents for Caries Prevention-Non-Fluoride Systems", Adv. Dent. Res., vol. No. 9, Issue No. 3, Nov. 1995, pp. 304-311.

Roberts, MJ et al., "Remineralisation of fluorotic enamel lesions by casein phosphopeptide-amorphous calcium fluorophosphate (CPP-ACFP) solution", IADR, ANZ Division, Abstract 54, 2000, 2 pages.

Robinson, C. et al., "Effect of Surface Zone Deproteinisation on the Access of Mineral Ions into Subsurface Carious Lesions of Human Enamel", Caries Res, vol. No. 24, 1990, pp. 226-230.

Rose, R.K., "Binding Characteristics of Streptococcus Mutans for Calcium and Casein Phosphopeptide", Caries. Res., vol. No. 34, 2000, pp. 427-431.

Rose, R.K., "Effects of an Anticariogenic Casein Phosphopeptide on Calcium Diffusion in Streptococcal Model Dental Plaques", Archives of Oral Biology, vol. No. 45, 2000, pp. 569-575.

Rosen, S. et al., "Effect of Cheese, With and Without Sucrose, on Dental Caries and Recovery of Streptococcus mutans in Rats", J. Dent. Res., vol. No. 63, Issue No. 6, Jun. 1984, pp. 894-896.

Rozwadowska, E., "Children and private dentistry", Private Dentistry, May 2006, pp. 109-113.

Sakaguchi, Y. et al. "Remineralization Potential of CPP-ACP and its Synergy with Fluoride", Abstract 0191, 84th General Session of the IADR, Jun. 28-Jul. 1, 2006, Brisbane, Australia, 3 pages.

Sakaguchi, Y. et al., "Preventing Acid Induced Enamel Demineralization Using CPP-ACP Containing Paste", Abstract 2055, IADR, Mar. 2005, Baltimore, Maryland, USA, 1 page.

(56) References Cited

OTHER PUBLICATIONS

Sakr, A.M. et al., "The Effect of Recaldent (CPP-ACP) on the most putative bacteria in caries and chronic gingivitis", Ain Shams Dental Journal, vol. No. X, Issue No. 2, Jun. 2007, pp. 211-219.
Sato, T. et al., "Caries Prevention Potential of a Tooth-coating Material Containing Casein Phosphopeptide-Amorphous Calcium Phosphate (CPP-ACP)," IADR, General Session, Goteborg, 2003, Abstract 1007, 3 pages.
Schüpbach, P. et al., "Incorporation of Caseinoglycomacropeptide and Caseinophosphopeptide into the Salivary Pellicle Inhibits Adherence of Mutans Streptococci", J. Dent. Res, vol. No. 75, Issue No. 10, Oct. 1996, pp. 1779-1788.
Schweigert, B.S. et al., "Dental Caries in the Cotton Rat—VI. The Effect of the Amount of Protein, Fat and Carbohydrate in the Diet on the Incidence and Extent of Carious Lesions", J. Nutr., vol. No. 31, 1946, pp. 439-447.
Shaw, J.H., "Effects of dietary composition on tooth decay in the albino rat", J. Nutr., vol. No. 41, 1950, pp. 13-23.
Sheharyar, S. et al., "Efficacy of MI Paste for Sensitivity Associated With Vital Bleaching", Abstract 2041, IADR, Mar. 2007, New Orleans, USA, 2 pages.
Shen, P. et al., "Enamel remineralization by a mouthrinse containing casein phosphopeptide-amorphous calcium phosphate and fluoride in an in situ model", Australian Dental Journal ADRF Special Research Supplement, vol. No. 49, Issue No. 4, 2004, p. S19.
Shen, P. et al., "Remineralization of Enamel Subsurface Lesions by Sugar-free Chewing Gum Containing Casein Phosphopeptide-Amorphous Calcium Phosphate", J Dent Res, vol. No. 80, Issue No. 12, 2001, pp. 2066-2070.
Shen, P. et at., "Remineralization by a Mouthrinse Containing CPP-ACP at pH 5.5", Abstract 0189, 84th General Session of the IADR, Jun. 28-Jul. 1, 2006, Brisbane, Australia, 1 page.
Silva, M. et al., "Fluoride content of infant formulae in Australia", Australian Dental Journal, vol. No. 41, Issue No. 1, 1996, pp. 37-42.
Silva, M.F. de A. et al., "Effects of Water-soluble Components of Cheese on Experimental Caries in Humans", J Dent Res, vol. No. 66, Issue No. 1, Jan. 1987, pp. 38-41.
Sim, C. et al., "Anti-caries effect of CPP-ACP in irradiated nasopharyngeal carcinoma patients", Clinical Oral Investigations, vol. No. 19, Issue No. 5, 2015, pp. 1005-1011.
Skold-Larsson, K. et al., "Fluoride concentration in plaque in adolescents after topical application of different fluoride varnishes", Clin Oral Invest., vol. No. 4, 2000, pp. 31-34.
Slomiany, B.L. et al., "Salivary Mucins in Oral Mucosal Defense", Gen. Pharmac., vol. No. 27, Issue No. 5, 1996, pp. 761-771.
Smith, S. et al., "Ultramorphological evaluation of dentin after treatment with different desensitizing agents", Abstract 0941, IADR, 2007, New Orleans, USA, 2 pages.
Smolenski, D. et al., "MI Paste and Fluoride for Caries Prevention In-Vitro", Abstract 0505, IADR, 2007, New Orleans, USA, 2 pages.
Steinberg, S., "A Modern Paradigm for Caries Management, Part 1: Diagnosis and Treatment", Dentistry Today, Feb. 2007, 11 pages.
Steinberg, S., "A Modern Paradigm for Caries Management, Part 2: A Practical Protocol", Dentistry Today, Jun. 2007, 6 pages.
Stößer, L., et al., "Kariesprotektive Eigenschaften des durch Caseinphosphopeptid stabilisierten amorphen Calciumphosphat-Nanokomplexes (CPP-ACP)", Deutsche Zahniirztliche Zeitschrift, vol. No. 62, Issue No. 9, 2008, pp. 579-588 (English Abstract).
Sudjalim, T.R. et al., "Prevention of demineralization around orthodontic brackets in vitro", American Journal of Orthodontics and Dentofacial Orthopedics., 2007, vol. No. 131, Issue No. 6, pp. 705.e1-705.e9.
Sudjalim, T.R. et al., "Prevention of white spot lesions in orthodontic practice: a contemporary review", Australian Dental Journal, vol. No. 51, Issue No. 4, 2006, pp. 284-289.
Sukasaem, H. et al., "Effect of CPP-ACP on Hardness of Enamel Eroded by Cola-drink", Abstract 1673, 84th General Session of the IADR, Jun. 28-Jul. 1, 2006, Brisbane, Australia, 1 page.
Supplementary European Search Report issued on Dec. 13, 2016 in EP Appl. Ser. No. EP14830019 (2 pages).
Takamizawa, T. et al., "Determination of Demineralization of Tooth Substrate by Use of an Ultrasonic Device", Japan J Conserv Dent, Jun. 47, Spring Issue 24, Abstract B-4, 2004, 2 pages.
Talbo, G.H. et al., "MALDI-PSD-MS Analysis of the Phosphorylation Sites of Caseinomacropeptide", Peptides, vol. No. 22, 2001, pp. 1093-1098.
Tantbirojn, D. et al., "Changes in surface hardness of enamel by a cola drink and a CPP-ACP paste", Journal of Dentistry, vol. No. 36, 2008, pp. 74-79.
Tay, L.Y. et al. "Assessing the Effect of a Desensitizing Agent Used Before In-office Tooth Bleaching," The Journal of the American Dental Association, vol. No. 140, Issue No. 10, Oct. 2009, pp. 1245-1251.
Ten Cate, J.M., "Current concepts on the theories of the mechanism of action of fluoride", Acta Odontol Scand, vol. No. 57, 1999, pp. 325-329.
Theerapiboon, U. et al., "Remineralization of Artificial Caries by CPP-ACP Paste", Abstract 3274, Jul. 2008, International Association for Dental Research, Toronto, Canada, 1 page.
Trajtenberg, C.P. et al., "CPP-ACP Paste with Fluoride: In Vitro Root Surface Caries Formation", Abstract 0500, IADR, 2007 New Orleans, USA, 2 pages.
Translation of Japanese Office Action from Application No. 2002-590925, Nov. 18, 2018.
Translation of Russian Office Action from Application No. 2007123603, May 26, 2009, 3 pages.
Turssi, C.P. et al., "Progression of erosion following use of calcium and phosphorus compounds", Abstract 2499, Jul. 2008, International Association for Dental Research, Toronto, Canada, 1 page.
Ung, M. et al. "Investigation of the binding of casein phosphopeptides to the major enamel pellicle proteins", Australian Dental Journal ADRF Special Research Supplement, vol. 49, Issue No. 4, 2004, pp. S19-S20.
Vegarud et al "Mineral-binding milk proteins and peptides; occurrence, biochemical and technological characteristics", British Journal of Nutrition (2000), vol. 84, Suppl. 1, p. S91-S98. (Year: 2000).
Vlacic, J. et al., "Combined CPP-ACP and photoactivated disinfection (PAD) therapy in arresting root surface caries: a case report", British Dental Journal, vol. No. 203, Issue No. 8, Oct. 27, 2007, pp. 457-459.
Walker, G. et al., "Increased remineralization of tooth enamel by milk containing added casein phosphopeptide-amorphous calcium phosphate", Journal of Dairy Research, vol. No. 73, 2006, pp. 74-78.
Walker, G.D. et al., "Consumption of milk with added casein phosphopeptide-amorphous calcium phosphate remineralizes enamel subsurface lesions in situ", Australian Dental Journal, vol. No. 54, Issue No. 3, Sep. 2009, pp. 245-249.
Walsh, L., "Clinical applications of Recaldent products: which ones to use where", Australasian Dental Practice, May/Jun. 2007, pp. 144-146.
Walsh, L., "Clinical Aspects of Salivary Biology for the Dental Clinician", International Dentistry SA, vol. No. 9, Issue No. 4, 2007, pp. 22-41.
Walsh, L., "Tooth Mousse Information", GC Tooth Mousse Portfolio, 2nd Edition, Mar. 2005, 17 pages.
Walsh, L., "Topical CPP-ACP cremes beyond caries prevention", International Dentistry South Africa, vol. No. 4, Issue No. 5, 2014, pp. 26-32.
Walsh, L.J. et al., "Effect of CPP-ACP versus Potassium Nitrate on Cervical Dentinal Hypersensitivity", Abstract 0947, 84th General Session of the IADR, Jun. 28-Jul. 1, 2006, Brisbane, Australia, 1 page.
Walsh, L.J., "Application of the System for Total Environmental Management (STEM) to dysmineralization, dental erosion and tooth wear", Australasian Dental Practice, Jan./Feb. 2008, pp. 52-58.
Walsh, L.J., "The effects of GC Tooth Mousse on cervical dentinal sensitivity: a controlled clinical trial", International Dentistry SA—Australasian Edition, vol. No. 5, Issue No. 1, 2010, 7 pages.
Weiss, V., "Kariesprophylaxe in der kinderzahnärztlichen Praxis", ZWP, Oct. 2005, pp. 76-79 (English Abstract).

(56) References Cited

OTHER PUBLICATIONS

Westerman, G. et al., "Argon Laser and Remineralizing Paste Effect on Root Surface Caries", Abstract 0018, IADR, Mar. 2007, New Orleans, USA, 2 pages.
Westerman, G. et al., "Argon Laser and Remineralizing Paste with Fluoride Effects on Enamel Caries," AAPD, Washington, 2008, 1 page.
White DJ. "A 'return' to stannous fluoride dentifrices," J Clin Dent. 1995; 6 Spec No. 29-36.
White, D.J., "Use of Synthetic Polymer Gels for Artificial Carious Lesion Preparation", Caries Research, vol. No. 21, Issue No. 3, 1987, pp. 228-242.
Wikiel, K. et al, "Hydroxyapatite Mineralization and Demineralization in the Presence of Synthetic Phosphorylated Pentapeptides", Archives of Oral Biology, vol. No. 39, Issue No. 8, 1994, pp. 715-721.
Willershausen, B. et al., "In-Vitro-Studie Zur Überprufung einer möglichen Remineralisation durch caesinphosphopetidhaltige, amorphe Calciumphosphat-komplexe (CPP ACP)", Deutsche Zahnarztliche Zeitschrift, vol. No. 63, Issue No. 2, 2008, pp. 134-139 (Eng Abstract).
William, V. et al., "Molar Incisor Hypomineralization: Review and Recommendations for Clinical Management", Pediatric Dentistry, vol. No. 28, Issue No. 3, 2006, pp. 224-232.
Wong, L. et al., "Plaque microcosm biofilm mineralisation by CPP-ACP and calcium-phosphate-monofluorophosphate-urea mineralising solution", Abstract 1269, 84th General Session of the IADR, Jun. 28-Jul. 1, 2006, Brisbane, Australia, 1 page.
Wong, R. et al., "Incorporation of Casein Phosphopeptide-Amorphous Calcium Phosphate into a Temporary Cement", Abstract 0653, 84th General Session of the IADR, Jun. 28-Jul. 1, 2006, Brisbane, Australia, 1 page.
Wright, S. et al., "Artificial Caries Inhibited with MI Paste and Two Restorative Materials", Abstract 2777, IADR, 2007, New Orleans, USA, 2 pages.
Xie, Q. et al., "Remineralization Effects of CPP-ACP and Proanthocyanidin on Artificial Root Caries", Abstract 0512, IADR, 2007, New Orleans, USA, 2 pages.
Yamaguchi, K. et al., "Effect of CPP-ACP paste on mechanical properties of bovine enamel as determined by an ultrasonic device", Journal of Dentistry, vol. No. 34, 2006, pp. 230-236.
Yamaguchi, K. et al., "Ultrasonic Determination of the Effect of Casein Phosphopeptide-Amorphous Calcium Phosphate Paste on the Demineralization of Bovine Dentin", Caries Res, vol. No. 41, 2007, pp. 204-207.
Ying, S.N. & Liu, L., "Research progress of enamel remineralization materials [J/CD]", Chin. J. Stomatol. Res. (Electronic version), vol. No. 5, Issue No. 1, 2011, pp. 94-99.
Zanatta, F. et al., "Supragingival Plaque Removal with and without Dentifrice: A Randomized Controlled Clinical Trial", Braz Dent J, vol. No. 23, Issue No. 3, 2012, pp. 235-240.
Zero, D.T., "Dentifrices, mouthwashes, and remineralization/caries arrestment strategies", BMC Oral Health, vol. No. 6, Suppl. I:S9, Jul. 2006, 13 pages.
Zero, D.T., "In situ Caries Models", Adv Dent Res, vol. No. 9, Issue No. 3, Nov. 1995, pp. 214-230.
Zhang et al., "Antioxidant Properties of Casein Phosphopeptides (CPP) and Maillard-Type Conjugated Products," Antioxidants: 9 (8): 648 (Jul. 22, 2020) (14 pgs).
Zhang, L. et al., "Experimental Study of Phosphopeptide in Promoting Tooth Remineralization", Chin J Dent Res., vol. No. 3, Issue No. 1, May 2000, pp. 27-30.
Zhao, Q. et al., "The remineralization for enamel lesions by casein phosphopeptide-amorphous calcium fluoride phospate in vitro", Zhonghua Kou Qiang Yi Xue Za Zhi, vol. No. 36, Issue No. 6, 2001, 8 pages.
Ajaj et al., "Effect of different acid etchants on the remineralization process of white-spot lesions: An in vitro study.", American Journal of Dentistry, Feb. 2020; pp. 43-47.
Fernando et al., "Self-assembly of dental surface nanofilaments and remineralisation by SnF2 and CPP-ACP nanocomplexes", Sci Rep, 2019; 9: 1285.
Gurunathan D et al., "Casein phosphopeptide-amorphous calcium phosphate: a remineralizing agent of enamel", Australian Dental Journal, 2012; 57: 404-408.
Hsu C.-Y.S et al., "Laser-Matrix-Fluoride Effects on Enamel Demineralization", Journal of Dental Research, Sep. 2001; vol. 80, No. 9, pp. 1797-1801.
Huang et al., "Remineralisation Effect of CPP-ACP and Diode Laser Stabilised by Case on the Initial Enamel caries of Primary Teeth", Progress in Modern Biomedicine, Jan. 2019; 19(2): 279.
Kshirsagar et al., "Comparative assessment of bond strengths of affected dentin, using two different remineralizing solutions with or without lasers: Results of an in vitro pilot study", SRM Journal of Research in Dental Sciences, Jan. 2015; vol. 6, No. 2.
L.J. Walsh "Clinical applications of Recaldent products: which ones to use where," Australasian Dental Practice, May/Jun. 2007, 144-146. (Year: 2007).
Sakr, A. K., ELkarargy, A. A. M., & Sherif, M. M. (2007). The Effect of Recaldent (CPP-ACP) on the most putative bacteria in caries and chronic gingivitis. Ain Shams Dental Journal, 211-219. (Year: 2007).
Verguard et al., "Mineral-binding milk proteins and peptides; occurrence, biochyemical and technological characteristics", British Journal of Nutrition, Nov. 2000; 84: Suppl. 1, S91-S98.
White, A return to stannous fluoride dentrifices, Journal of clinical dentistry, Feb. 1995; Spec No. 29-36.

COMPOSITIONS AND METHODS FOR DENTAL MINERALIZATION

CROSS-REFERENCE TO RELATED APPLICATIONS

The present application is a continuation of U.S. application Ser. No. 17/832,556 filed Jun. 3, 2022 (now U.S. Pat. No. 11,717,537), which is a continuation of U.S. application Ser. No. 16/852,983 filed Apr. 20, 2020 (now U.S. Pat. No. 11,351,193), which is a continuation of U.S. application Ser. No. 14/906,395, filed Jan. 20, 2016 (now U.S. Pat. No. 10,695,370), which is the U.S. National Stage of International Application No. PCT/AU2014/050144, filed Jul. 23, 2014, and claims priority to Australian Patent Application No. 2013902815, filed Jul. 23, 2013.

FIELD OF THE INVENTION

The present invention relates to compositions for mineralizing a dental surface, in particular tooth enamel. Methods of mineralizing hypomineralized lesions (including subsurface lesions) in the tooth enamel caused by various conditions such as dental caries, dental corrosion and fluorosis are also provided.

BACKGROUND OF THE INVENTION

Common causes of hypomineralized lesions are caries and fluorosis.

Dental caries result from the demineralization of hard tissue of the teeth usually because of fermentation of dietary sugar by dental plaque odontopathogenic bacteria. Dental caries is still a major public health problem. Further, restored tooth surfaces can be susceptible to further dental caries around the margins of the restoration. Even though the prevalence of dental caries has decreased through the use of fluoride in most developed countries, the disease remains a major public health problem. Dental erosion or corrosion is the loss of tooth mineral by dietary or regurgitated acids. Dental hypersensitivity is due to exposed dentinal tubules through loss of the protective mineralized layer, cementum. Dental calculus is the unwanted accretion of calcium phosphate minerals on the tooth surface. All these conditions, dental caries, dental erosion, dental hypersensitivity and dental calculus are therefore imbalances in the level of calcium phosphates.

Enamel fluorosis (mottling) has been recognized for nearly a century, however, the aetiological role of fluoride was not identified until 1942. The characteristic appearance of fluorosis may be differentiated from other enamel disturbances. The clinical features of fluorotic lesions of enamel (FLE) represent a continuum ranging from fine opaque lines following the perikymata, to chalky, white enamel. The presence of a comparatively highly mineralized enamel outer surface and a hypomineralized subsurface in the fluorotic lesion simulates the incipient enamel "white spot" carious lesion. With increasing severity, both the depth of enamel involved in the lesion and the degree of hypomineralization increases. The development of fluorosis is highly dependent on the dose, duration and timing of fluoride exposure and is believed to be related to elevated serum fluoride concentrations. Chalky "white spot" lesions may also form on developing teeth in children such as after treatment with antibiotics or fever. Such lesions indicate areas of hypomineralization (i.e. too little mineralization) of the tooth enamel.

Depending on lesion severity, fluorosis has been managed clinically by restorative replacement or micro-abrasion of the outer enamel. These treatments are unsatisfactory because they involve restorations or removal of tooth tissue. What is desired is a treatment that will mineralize the hypomineralized enamel to produce a natural appearance and structure.

Specific complexes of casein phosphopeptides and amorphous calcium phosphate ("CPP-ACP", available commercially as Recaldent®) have been shown to remineralize enamel subsurface lesions in vitro and in situ (Reynolds, 1998; Shen et al., 2001; Reynolds et al., 2003).

WO 98/40406 in the name of The University of Melbourne (the contents of which are herein incorporated fully by reference) describes casein phosphopeptide-amorphous calcium phosphate complexes (CPP-ACP) and CPP-stabilized amorphous calcium fluoride phosphate complexes (CPP-ACFP) which have been produced at alkaline pH. Such complexes have been shown to prevent enamel demineralization and promote remineralization of enamel subsurface lesions in animal and human in situ caries models (Reynolds, 1998). Improved casein phosphopeptide-amorphous calcium phosphate complexes (CPP-ACP) and CPP-stabilized amorphous calcium fluoride phosphate complexes (CPP-ACFP) have also been described in WO2006/056013 and WO2006/135982.

The CPP which are active in forming the complexes do so whether or not they are part of a full-length casein protein. Examples of active (CPP) that can be isolated after tryptic digestion of full length casein have been specified in U.S. Pat. No. 5,015,628 and include peptides Bos $\alpha_{s1}$-casein X-5P (f59-79), Bos β-casein X 4P (f1-25), Bos $\alpha_{s2}$-casein X-4P (f46-70) and Bos $\alpha_{s2}$-casein X-4P (f1-21).

There is a need to provide improved or alternative treatments for hypomineralized lesions.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In one aspect, the present invention provides a method of mineralizing a dental surface or subsurface comprising contacting the dental surface or subsurface with a compound that is capable of increasing or maintaining the pH of a solution and a mineralizing agent. Preferably, the mineralizing agent is stabilized amorphous calcium phosphate (ACP) and/or amorphous calcium fluoride phosphate (ACFP). Typically, the compound is capable of maintaining the pH of a solution between 7 to 9, preferably about 7.5. Preferably, the compound is provided in an amount effective to raise the pH of intra-lesion fluid of a dental lesion from 6 to 7.5. The compound is capable of increasing the pH of a solution that has an acidic pH (i.e. less than pH 7). The dental surface is preferably dental enamel. In one embodiment the dental surface is a lesion in the enamel, such as a lesion caused by caries, dental erosion or fluorosis.

A compound which is capable of increasing or maintaining the pH of a solution includes a compound which can accept hydrogen cations (protons) or, more generally, donate a pair of valence electrons. Preferably, the compound is a base. The compound may not necessarily normally be regarded as a base, for example a polypeptide with numerous acidic and basic residues but nonetheless has the ability to maintain or increase the pH of a solution between 7 to 9, preferably 7.5. The compound is capable of increasing the pH of a solution that has an acidic pH (i.e. less than pH 7). For example, the compound is capable of increasing the pH of the acidic intra-lesion fluid of a subsurface lesion requiring remineralisation. Preferably, the compound is provided in an amount effective to raise the pH of intra-lesion fluid of a dental lesion from 6 to 7.5. In one embodiment, a compound which is capable of increasing or maintaining the pH of a solution is an alkali which has the capacity to release hydroxide ions.

A compound which is capable of increasing or maintaining the pH of a solution also includes a compound that can maintain as a buffer the pH of a neutral or basic solution (i.e. pH greater than or equal to 7) when the neutral or basic solution is exposed to an acid. Typically, the compound is capable of maintaining the pH of a solution between 7 to 9, preferably about 7.5.

Any pharmaceutically acceptable compounds described as a base are suitable for use in the invention. Typically, the base is suitable for oral use. Preferably, the compound acts as a base, i.e. only releases hydroxide ions or donates electrons, in the presence of an acid. The base may be a free-base form, or in a pharmaceutically acceptable salt form. Non-limiting examples of bases suitable for use in the invention include hydroxides, chlorides, borates, phosphates including hydrogen phosphates and dihydrogen phosphates, citrates, carbonates, bicarbonates, hypochlorites (such as sodium hypochlorite), amines and any salt forms thereof including an alkali metal salt forms. More specifically, non-limiting examples of suitable pharmaceutically acceptable bases include ammonium hydroxide, sodium hydroxide, potassium hydroxide, lithium hydroxide, calcium hydroxide, magnesium hydroxide, ferrous hydroxide, zinc hydroxide, sodium hypochlorite, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine or urea. A hypofluorite capable of acting as a base as described herein is also useful in the invention as the agent for increasing or maintaining pH. A suitable hypofluorite would react in situ, being a surface or subsurface lesion, to produce fluoride ions and hydroxide (or another base) ions. As one skilled in the art will appreciate a potentially favourable outcome of the production of fluoride ions is that fluoride ions can substitute for hydroxide in the crystal structure of apatite forming fluorapatite.

Preferably the ACP and/or ACFP is phosphopeptide (PP)-stabilized. Preferably, the phosphopeptide (as defined below) is a casein phosphopeptide. Preferably, the ACP or ACFP is in the form of a casein phosphopeptide stabilized ACP or ACFP complex.

In a preferred embodiment, the phosphopeptide stabilized amorphous calcium phosphate (ACP) or amorphous calcium fluoride phosphate (ACFP) complex has tightly bound and loosely bound calcium, wherein the tightly bound calcium in the complex is less than the tightly bound calcium in an ACP or ACFP complex formed at a pH of 7.0. Optionally, the ACP or ACFP is predominantly in a basic form.

In a preferred embodiment, the calcium ion content of the stabilized ACP or ACFP complex is in the range of about 30 to 100 moles of calcium per mole of PP. More preferably, the calcium ion content is in the range of about 30 to about 50 moles of calcium per mole of PP.

In any aspect or embodiments as described herein, the stabilized ACP and/or ACFP may be in a formulation with additional calcium phosphate. Typically, the formulation includes a PP stabilized ACP and/or ACFP complex together with at least an equal amount by weight of calcium phosphate.

In a preferred embodiment the ACP and/or ACFP is in the form of a casein phosphopeptide stabilized ACP and/or ACFP complex.

Preferably, the phase of the ACP is predominantly a basic phase, wherein the ACP comprises predominantly the species $Ca^{2+}$, $PO_4^{3-}$ and $OH^-$. The basic phase of ACP may have the general formula $[Ca_3(PO_4)_2]_x[Ca_2(PO_4)(OH)]$ where $x \geq 1$. Preferably $x=1-5$. More preferably, $x=1$. Preferably the two components of the formula are present in equal proportions. Accordingly, in one embodiment, the basic phase of ACP has the formula $Ca_3(PO_4)_2Ca_2(PO_4)(OH)$.

Preferably, the phase of the ACFP is predominantly a basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)F]_y$ where $x \geq 1$ when $y=1$ or where $y \geq 1$ when $x=1$. Preferably, $y=1$ and $x=1-3$. More preferably, $y=1$ and $x=1$. Preferably the two components of the formula are present in equal proportions.

Accordingly, in one embodiment, the basic phase of ACFP has the formula $Ca_3(PO_4)_2Ca_2(PO_4)F$.

In one embodiment, the ACP complex consists essentially of phosphopeptides, calcium, phosphate and hydroxide ions and water.

In one embodiment, the ACFP complex consists essentially of phosphopeptides, calcium, phosphate, fluoride and hydroxide ions and water.

In a further aspect of the present invention there is provided a method of mineralizing a dental surface comprising providing a compound which is capable of increasing or maintaining the pH of a solution and a source of ACP or ACFP. In a preferred embodiment the dental surface is enamel. Preferably the compound which is capable of increasing or maintaining the pH of a solution is a base. The base may be any base described herein, including, but not limited to, sodium bicarbonate, sodium hypochlorite, a hypofluorite or urea.

In a further aspect of the present invention there is provided a method for treating fluorosis comprising contacting a fluorotic lesion in tooth enamel with a compound which is capable of increasing or maintaining the pH of a solution and stabilized ACP and/or ACFP. Preferably the compound which is capable of increasing or maintain the pH of a solution is a base. The base may be any base described herein, including, but not limited to, sodium bicarbonate, sodium hypochlorite, a hypofluorite or urea.

In a further aspect of the present invention there is provided a method for treating dental caries comprising contacting a caries lesion in tooth enamel with a compound which is capable of increasing or maintaining the pH of a solution and stabilized ACP and/or ACFP. Preferably the compound which is capable of increasing or maintain the pH of a solution is a base. The base may be any base described herein, including, but not limited to, sodium bicarbonate, sodium hypochlorite, a hypofluorite or urea.

In a further aspect of the present invention there is provided a method for treating dental erosion comprising contacting a lesion in tooth enamel caused by erosion with a compound which is capable of increasing or maintaining the pH of a solution and stabilized ACP and/or ACFP. Preferably the compound which is capable of increasing or maintain the pH of a solution is a base. The base may be any base described herein, including, but not limited to, sodium bicarbonate, sodium hypochlorite, a hypofluorite or urea.

In a further aspect of the present invention there is provided a method for reducing white spot lesions on the tooth enamel comprising contacting a white spot lesion with a compound which is capable of increasing or maintaining the pH of a solution and stabilized ACP and/or ACFP. Preferably the compound which is capable of increasing or maintain the pH of a solution is a base. The base may be any base described herein, including, but not limited to, sodium bicarbonate, sodium hypochlorite, a hypofluorite or urea.

In a further aspect of the present invention there is provided a method for remineralizing a lesion in tooth enamel comprising contacting the lesion with a compound which is capable of increasing or maintaining the pH of a solution and stabilized ACP and/or ACFP. Preferably the compound which is capable of increasing or maintain the pH of a solution is a base. The base may be any base described herein, including, but not limited to, sodium bicarbonate, sodium hypochlorite, a hypofluorite or urea.

In a further aspect of the invention there is provided a method for remineralizing a lesion in tooth enamel comprising contacting the lesion with stabilized ACP and/or ACFP followed by administering a composition containing sodium bicarbonate or urea. Preferably, the composition is a mouthrinse or mouthwash containing sodium bicarbonate or urea.

In one embodiment, the compound which is capable of increasing or maintaining the pH of a solution is not sodium hypochlorite (NaOCl) and a composition of the invention is sodium hypochlorite (NaOCl) free.

In any aspect or embodiment of the invention described herein, the compound which is capable of increasing or maintaining the pH of a solution is administered concurrently with, as a pre-treatment to, or as a post-treatment to a source of stabilized ACP or ACFP. Preferably the compound which is capable of increasing or maintain the pH of a solution is a base. The base may be any base described herein, including, but not limited to, sodium bicarbonate, sodium hypochlorite, a hypofluorite or urea.

In any aspect or embodiment of the invention described herein, the compound which is capable of increasing or maintaining the pH of a solution is administered concurrently with or as a post-treatment to a source of stabilized ACP or ACFP. Preferably the compound which is capable of increasing or maintain the pH of a solution is a base. The base may be any base described herein, including, but not limited to, sodium bicarbonate, sodium hypochlorite, a hypofluorite or urea.

In any aspect or embodiment of the invention described herein, the compound which is capable of increasing or maintaining the pH of a solution and stabilized ACP or ACFP is applied to the mouth, tooth or lesion by the subject in need of treatment or by a dental health care professional.

In any aspect or embodiment of the invention described herein, the ACP and/or ACFP is phosphopeptide (PP)-stabilized. Preferably, the phosphopeptide (as defined below) is a casein phosphopeptide. Preferably, the ACP or ACFP is in the form of a casein phosphopeptide stabilized ACP or ACFP complex.

The compound which is capable of increasing or maintaining the pH of a solution may be contacted with the dental surface for a period of about 1 to 60 minutes, or for about 1 to 30 minutes. In one embodiment, the compound which is capable of increasing or maintaining the pH of a solution is contacted with the dental surface for about 20 minutes.

Preferably the stabilized ACP and/or ACFP are contacted with the dental surface for a period of about 1 minute to 2 hours, or 5 minutes to 60 minutes or about 10 minutes. The stabilized ACP and/or ACFP may be repeatedly applied to the dental surface over a period of 1 day to several months.

In one embodiment, the compound which is capable of increasing or maintaining the pH of a solution is contacted with the dental surface 1 to 60 minutes, or 1 to 30 minutes, or 1 to 5 minutes prior to contacting the dental surface with the stabilized ACP and/or ACFP.

In one embodiment, the compound which is capable of increasing or maintaining the pH of a solution is contacted with the dental surface 1 to 60 minutes, or 1 to 30 minutes, or 1 to 5 minutes after contacting the dental surface with the stabilized ACP and/or ACFP.

In a further aspect of the present invention there is provided a method for mineralizing a tooth surface comprising applying a stabilized ACP and/or ACFP complex and a compound which is capable of increasing or maintaining the pH of a solution to a tooth surface. Preferably the tooth surface is tooth enamel. Typically, the tooth surface is tooth enamel containing a lesion selected from the group consisting of one or more of a white spot lesion; a fluorotic lesion; a caries lesion; or a lesion caused by tooth erosion. Preferably, the stabilized ACP and/or ACFP complex and a compound which is capable of increasing or maintaining the pH of a solution is contained in the same composition that is applied to the tooth surface. Preferably the compound which is capable of increasing or maintain the pH of a solution is a base. The base may be any base described herein, including, but not limited to, sodium bicarbonate, sodium hypochlorite, a hypofluorite or urea.

In one embodiment, the dental surface is in need of such treatment. Therefore the invention includes in addition to the steps of any method described herein a step of identifying a subject suffering fluorosis, dental caries, dentinal hypersensitivity or dental calculus, a white spot lesion; a fluorotic lesion; a caries lesion; or a lesion caused by tooth erosion.

In one aspect, the present invention provides a composition for mineralizing a dental surface or subsurface comprising a compound that is capable of increasing or maintaining the pH of a solution and a mineralizing agent. Preferably, the mineralizing agent is stabilized amorphous calcium phosphate (ACP) and/or amorphous calcium fluoride phosphate (ACFP). Preferably, the compound is capable of increasing or maintaining the pH of a solution is present in an amount effective to raise the pH of a dental lesion from 6.0 to 7.5. Preferably, the compound that is capable of increasing or maintaining the pH of a solution is any one or more of the compounds described herein, preferably a base. The base may be any base described herein, including, but not limited to, sodium bicarbonate, sodium hypochlorite, a hypofluorite or urea.

Any composition described herein may be a physiologically acceptable composition formulated as a toothpaste, toothpowder, liquid dentifrice, mouthwash, mouthrinse, mouth spray, varnish, dental cement, troche, chewing gum, lozenge, dental paste, gingival massage cream, gargle tablet, dairy product and other foodstuffs.

Any composition described herein can be used in any one of the methods described herein. The composition is a physiologically acceptable composition as described herein.

In another aspect, the present invention provides a composition comprising a compound that is capable of increasing or maintaining the pH of a solution and a mineralizing agent for use in mineralizing a dental surface or subsurface. Preferably, the mineralizing agent is stabilized amorphous calcium phosphate (ACP) and/or amorphous calcium fluoride phosphate (ACFP). Preferably the compound which is capable of increasing or maintain the pH of a solution is a base. The base may be any base described herein, including, but not limited to, sodium bicarbonate, sodium hypochlorite, a hypofluorite or urea.

In a further aspect, there is provided a method of treating or preventing one or more of each of dental caries, tooth decay, dental erosion and fluorosis, comprising the steps of administering a compound capable of increasing or maintaining the pH of a solution to the teeth of a subject followed by administering an ACP or ACFP complex or composition. Topical administration of the complex is preferred. The method preferably includes the administration of the complex in a formulation as described above. Preferably the compound which is capable of increasing or maintain the pH of a solution is a base. The base may be any base described herein, including, but not limited to, sodium bicarbonate, sodium hypochlorite, a hypofluorite or urea.

In a further aspect there is provided the use of a compound capable of increasing or maintaining the pH of a solution and a stabilized amorphous calcium phosphate (ACP) or amorphous calcium fluoride phosphate (ACFP) in the manufacture of a composition for the treatment and/or prevention of one or more of dental caries, tooth decay, dental erosion and fluorosis. Preferably the compound which is capable of increasing or maintain the pH of a solution is a base. The base may be any base described herein, including, but not limited to, sodium bicarbonate, sodium hypochlorite, a hypofluorite or urea.

In a further aspect there is provided a composition comprising as an active agent a compound capable of increasing or maintaining the pH of a solution and a stabilized amorphous calcium phosphate (ACP) or amorphous calcium fluoride phosphate (ACFP) for mineralizing a dental surface or subsurface. Typically, mineralizing a dental surface or subsurface is for the treatment and/or prevention of one or more of dental caries, tooth decay, dental erosion and fluorosis.

In any method or use of the invention there is further provided a step of applying a source of fluoride ions. The source of fluoride ions may be applied simultaneously as the compound which is capable of increasing or maintaining the pH of a solution and the source of ACP or ACFP. Alternatively, the source of fluoride ions may be applied prior to, or after, the compound which is capable of increasing or maintaining the pH of a solution, or the source of ACP or ACFP.

The present invention also provides a composition comprising a compound that is capable of increasing or maintaining the pH of a solution and a mineralizing agent. Preferably, the mineralizing agent is stabilized-amorphous calcium phosphate (ACP) or amorphous calcium fluoride phosphate (ACFP). Preferably, the composition further includes a pharmaceutically acceptable carrier, diluent or excipient. Preferably the compound which is capable of increasing or maintaining the pH of a solution is a base.

The base may be any base described herein, including, but not limited to, sodium bicarbonate, sodium hypochlorite, a hypofluorite or urea.

In a preferred embodiment of each aspect of the invention, the phosphopeptide stabilized amorphous calcium phosphate (ACP) or amorphous calcium fluoride phosphate (ACFP) complex in the composition has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

In another preferred embodiment of each aspect of the invention, the calcium ion content of the stabilized ACP or ACFP complex in the composition is in the range of about 30 to 100 moles of calcium per mole of PP. More preferably, the calcium ion content is in the range of about 30 to about 50 moles of calcium per mole of PP.

In any embodiment, the ACP and/or ACFP in the composition can be in the form of a casein phosphopeptide stabilized ACP and/or ACFP complex.

In another aspect the invention is a physiologically acceptable composition including stabilized amorphous calcium phosphate (ACP) and/or amorphous calcium fluoride phosphate (ACFP) as described herein, a base and an excipient, diluent or carrier suitable for oral administration. The base may be any base described herein, including, but not limited to, sodium bicarbonate, sodium hypochlorite, a hypofluorite or urea.

The invention also relates to a kit for the treatment or prevention of one or more of dental caries, fluorosis and dental erosion including (a) a compound capable of increasing or maintaining the pH of a solution and (b) a stabilized-ACP and/or stabilized-ACFP complex in a pharmaceutically acceptable carrier. Desirably, the kit further includes instructions for their use for the mineralization of a dental surface in a patient in need of such treatment. The instructions may describe the use of the kit to treat or prevent one or more of each of dental caries, tooth decay, dental erosion and fluorosis. In one embodiment, the agent and the complex are present in suitable amounts for treatment of a patient. Preferably, the stabilized ACP and/or ACFP is phosphopeptide (PP)-stabilized. Preferably, the phosphopeptide (as defined below) is a casein phosphopeptide. Preferably, the ACP or ACFP is in the form of a casein phosphopeptide stabilized ACP or ACFP complex.

The composition or kit of the invention may further include a source of fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride, silver fluoride, amine fluoride or any metal ion fluoride salt. A source of fluoride ions may be a hypofluorite. These sources of fluoride ions may be provided in solution (typically an aqueous solution), or a suspension.

DETAILED DESCRIPTION OF THE EMBODIMENTS

Further aspects of the present invention and further embodiments of the aspects described in the preceding paragraphs will become apparent from the following description, given by way of example and with reference to the accompanying drawings. It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include" can be used interchangeably.

In one aspect, the present invention provides a method of mineralizing a dental surface or subsurface comprising contacting the dental surface or subsurface with a compound that is capable of increasing or maintaining the pH of a solution and a mineralizing agent. A dental subsurface is typically a hypomineralized lesion such that the compound and mineralizing agent contacted to the dental surface migrates through any surface layer, i.e. pellicle and/or plaque, through the porous dental surface to the region requiring mineralization. Preferably, the mineralizing agent is stabilized amorphous calcium phosphate (ACP) and/or amorphous calcium fluoride phosphate (ACFP). The dental surface is preferably dental enamel. The dental surface may be a lesion in the enamel, such as a lesion caused by caries, dental erosion or fluorosis.

Any compound that is capable of increasing or maintaining the pH of a solution can be used in the method of the present invention. Without being bound by any theory or mode of action it is believed that the maintenance of a basic pH during intra-lesion mineralization minimises any restriction on the mineralization process by any acidic molecular species. Therefore, it is believed that the compound which is capable of increasing or maintaining the pH of a solution promotes mineralization by neutralising acid produced during the mineralization process.

Mineralization of dental surfaces can be significantly enhanced by increasing the pH of a lesion during the process of mineralization. In particular, it has been found that the mineralization of enamel by stabilized soluble forms of ACP (CPP-ACP) and ACFP (CPP-ACFP) is enhanced by a compound that increases the intra-lesion pH if the intra-lesion pH is acidic or maintains the intra-lesion pH if the intra-lesion pH is neutral or basic. For example, during the development of caries, the pH of the intra-lesion fluid may be 6 or below. The compound one that can raise, or maintain, the pH at which remineralization of a hypomineralised surface or subsurface can occur.

The compound which is capable of increasing or maintaining the pH of a solution may be contacted with the dental surface for a period of about 1 to 60 minutes, or for about 1 to 30 minutes. In one embodiment, the compound which is capable of increasing or maintaining the pH of a solution is contacted with the dental surface for about 20 minutes. An example of how this is achieved is formulating the compound into an oral composition, such as a paste, and then contacting or applying the composition to the dental surface. The oral composition, such as a paste, has sufficient viscosity to be retained on the tooth for the required time period.

Preferably the stabilized ACP and/or ACFP is contacted with the dental surface for a period of about 1 minute to 2 hours, or 5 minutes to 60 minutes or about 10 minutes. The stabilized ACP and/or ACFP may be repeatedly applied to the dental surface over a period of 1 day to several months.

In one embodiment, the compound which is capable of increasing or maintaining the pH of a solution is contacted with the dental surface 1 to 60 minutes, or 1 to 30 minutes, or 1 to 5 minutes prior to contacting the dental surface with the stabilized ACP and/or ACFP.

In one embodiment, the compound which is capable of increasing or maintaining the pH of a solution is contacted with the dental surface 1 to 60 minutes, or 1 to 30 minutes, or 1 to 5 minutes after contacting the dental surface with the stabilized ACP and/or ACFP.

In a further aspect of the present invention there is provided a method for mineralizing a tooth surface comprising applying an ACP and/or ACFP complex and a compound which is capable of increasing or maintaining the pH of a solution to a tooth surface. Preferably the tooth surface is tooth enamel. Typically, the tooth surface is tooth enamel containing a lesion selected from the group consisting of one or more of a white spot lesion; a fluorotic lesion; a caries lesion; or a lesion caused by tooth erosion.

In one embodiment, the dental surface is in need of such treatment. Therefore, in another aspect, the invention includes in addition to the steps of any method described herein a step of identifying a subject suffering fluorosis, dental caries, dentinal hypersensitivity or dental calculus, a white spot lesion; a fluorotic lesion; a caries lesion; or a lesion caused by tooth erosion.

In another aspect, the present invention provides a composition comprising a compound that is capable of increasing or maintaining the pH of a solution and a mineralizing agent for use in mineralizing a dental surface or subsurface.

A compound which is capable of increasing or maintaining the pH of a solution includes a compound which can accept hydrogen cations (protons) or, more generally, donate a pair of valence electrons. Preferably, the compound may commonly be a base. The compound is capable of increasing the pH of a solution that has an acidic pH (i.e. less than pH 7). Preferably, the compound is capable of raising the pH of intra-lesion fluid of a dental lesion from 6 to 7.5. In one embodiment, a compound which is capable of increasing or maintaining the pH of a solution is an alkali which has the capacity to release hydroxide ions.

A compound which is capable of increasing or maintaining the pH of a solution also includes a compound that can maintain as a buffer the pH of a neutral or basic solution (i.e. pH greater than or equal to 7) when the neutral or basic solution is exposed to an acid. Typically, the compound is capable of maintaining the pH of a solution between 7 to 9, preferably about 7.5. As used herein reference to the increasing or maintaining the pH of a solution includes increasing or maintaining the pH the fluid in a subsurface lesion, i.e. intra-lesion fluid.

Any pharmaceutically acceptable compounds described as a base are suitable for use in the invention. Typically, the base is suitable for oral use. Preferably, the compound acts as a base, i.e. only releases hydroxide ions or donates electrons, in the presence of an acid. The base may be a free-base form, or in a pharmaceutically acceptable salt form. Non-limiting examples of bases suitable for use in the invention include hydroxides, chlorides, borates, phosphates including hydrogen phosphates and dihydrogen phosphates, citrates, carbonates, bicarbonates, hypochlorites, amines and any salt forms thereof including an alkali metal salt forms.

More specifically, non-limiting examples of suitable pharmaceutically acceptable bases include ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine. A hypofluorite capable of acting as a base as described herein is also useful in the invention as the agent for increasing or maintaining pH. A suitable hypofluorite would react in situ to produce fluoride ions and hydroxide (or another base) ions. One skilled in the art will appreciate that fluoride ions can substitute for hydroxide in the crystal structure of apatite forming fluorapatite.

A stabilized-ACP or ACFP complex as described in the current specification may be the "closed" complexes are shown in FIG. 2 of Cross et al., 2007 *Current Pharmaceutical Design*, 13, 793-800.

A stabilized-ACP or ACFP complex as referred to herein includes a stabilized-ACP or ACFP complex as described in WO2006/056013 the contents of which are incorporated by reference.

In a preferred embodiment, the phosphopeptide stabilized amorphous calcium phosphate (ACP) or amorphous calcium fluoride phosphate (ACFP) complex has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

A stabilized-ACP or ACFP complex as referred to herein include a stabilized-ACP or ACFP complex formed at a pH of below 7.0. Preferably the complex is formed at a pH in the range of about 5.0 up to but below 7.0. More preferably the complex is formed at a pH range of about 5.0 to about 6.0. In a preferred embodiment, the complex is formed at a pH of about 5.0 or about 5.5. Preferably, the ACP or ACFP in the complex is predominantly in a basic form.

A stabilized-ACP may be produced by a method comprising the steps of:
(i) obtaining a solution comprising at least one phosphopeptide and;
(ii) admixing solutions comprising calcium ions, phosphate ions and hydroxide ions, while maintaining the pH at about 7.0 or below.

A stabilized ACFP may be produced by a method comprising the steps of:
(i) obtaining a solution comprising at least one phosphopeptide and;
(ii) admixing solutions comprising calcium ions, phosphate ions, hydroxide ions and fluoride ions, while maintaining the pH at about 7.0 or below.

The hydroxide ions may be titrated into the solution to maintain the phosphopeptide solution at an essentially constant pH. The calcium and phosphate ions may be titrated into the phosphopeptide solution with constant mixing and at a rate that avoids the formation of a calcium phosphate precipitate in the phosphopeptide solution.

A phosphopeptide stabilized amorphous calcium phosphate (ACP) or amorphous calcium fluoride phosphate (ACFP) complex may also include wherein the ACP in the complex has tightly bound and loosely bound calcium, wherein the tightly bound calcium in the complex is less than the tightly bound calcium in an ACP or ACFP complex formed at a pH of 7.0 and the ACP or ACFP is predominantly in a basic form, obtainable or obtained by a method comprising:
a) admixing a first solution comprising calcium ions, a second solution comprising phosphate ions, and optionally a third solution comprising fluoride ions, to a solution comprising phosphopeptides and a solvent with a pH of from about 5 up to but below 7; and
b) maintaining the pH of the solution at about 5.0 up to but below 7.0 during the admixing by adding hydroxide ions.

"Tightly" and "loosely" bound calcium and phosphate can be determined using analytical ultrafiltration as shown in Example 2. Briefly, the solution of phosphopeptide, calcium, phosphate and optionally fluoride admixed while maintaining the pH at about 7.0 or below can be first filtered through a 0.1 micron filter to remove free calcium and phosphate that is not associated with the complexes. This free calcium and phosphate is present in the filtrate and discarded. Any free calcium or phosphate that is not associated in any way with the complexes would not be bioavailable, i.e. delivered by the phosphopeptide to the tooth. The retentate from the 0.1 micron filtration can be further analyzed by centrifugation through a 3000 mw cutoff filter at 1,000 g for 15 min. The resulting filtrate contains calcium and phosphate that is loosely bound or associated with the complexes. At this centrifugal force calcium and phosphate that is not tightly bound to the complexes are released and move into the filtrate. The calcium and phosphate that is tightly bound in the complexes is retained in the retentate. The amount of tightly bound calcium and phosphate in the retentate can then be determined by subtracting the amount of calcium and phosphate in the filtrate from the total amount of calcium and phosphate in the retentate of the 0.1 micron filtration.

A stabilized-ACP or ACFP complex as referred to herein include a stabilized-ACP or ACFP complex as described in WO2006/135982 the contents of which are incorporated by reference.

A "superloaded" phosphopeptide or phosphoprotein (PP) is a phosphopeptide or phosphoprotein that has been superloaded with calcium and phosphate ions. The calcium ions of the superloaded PP may be in the range 30-1000 mol Ca per mole of PP, or in the range of 30-100 or 30-50 mole Ca per mole of PP. In another embodiment, the mol Ca per mol of PP is at least 25, 30, 35, 40, 45 or 50. It can be a stabilized-amorphous calcium phosphate (ACP) or amorphous calcium fluoride phosphate (ACFP) complex. The complex may be formed at any pH (eg 3-10). Preferably the phosphopeptide includes the sequence -A-B-C-, where A is a phosphoamino acid, preferably phosphoserine, B is any amino acid including a phosphoamino acid and C is glutamic acid, aspartic acid or a phosphoamino acid. The phosphoamino acid may be phosphoserine.

In one aspect, the present invention includes a phosphopeptide or phosphoprotein (PP) stabilized amorphous calcium phosphate or amorphous calcium fluoride phosphate complex having a calcium ion content greater than about 30 moles of calcium per mole of PP. In a preferred embodiment, the calcium ion content is in the range of about 30 to 100 moles of calcium per mole of PP. More preferably, the calcium ion content is in the range of about 30 to about 50 moles of calcium per mole of PP.

The invention also provides a phosphopeptide or phosphoprotein (PP) stabilized-amorphous calcium phosphate (ACP) or amorphous calcium fluoride phosphate (ACFP) complex produced by a method comprising the steps of:

(i) obtaining solutions comprising calcium, inorganic phosphate and fluoride (optional); and
(ii) admixing (i) with a solution comprising PP-ACP.

In a preferred embodiment, the PP is casein phosphopeptide (CPP).

In a further aspect, the present invention also includes use of a formulation of a PP stabilized ACP and/or ACFP complex together with at least an equal amount by weight of calcium phosphate. Preferably the calcium phosphate is $CaHPO_4$ or calcium lactate or any other soluble calcium phosphate compound. Preferably, the calcium phosphate (e.g. $CaHPO_4$) is dry blended with the PP stabilized ACP and/or ACFP complex. In a preferred embodiment, the PP-ACP and/or PP-ACFP complex: calcium phosphate ratio is about 1:1-50. more preferably about 1: 1-25, more preferably about 1:5-15. In one embodiment, the PP-ACP and/or PP-ACFP complex: calcium phosphate ratio is about 1:10.

The oral care formulation that includes a phosphopeptide or phosphoprotein (PP) stabilized amorphous calcium phosphate (ACP) and/or amorphous calcium fluoride phosphate (ACFP) complex having a calcium ion content greater than about 30 moles of calcium per mole of PP when used in the oral cavity may be produced by a method including the steps of:
(i) obtaining a powder including a PP-ACP and/or PP-ACFP complex;
(ii) dry blending with an effective amount of calcium phosphate; and
(iii) formulating the dry blended PP-ACP and/or PP-ACFP and calcium phosphate mixture into an oral care formulation.

Preferably, the form of calcium phosphate for dry blending is any soluble calcium phosphate including, but not limited to, $CaHPO_4$, $Ca_2HPO_4$ and calcium lactate.

The present invention also provides a method of mineralizing a dental surface or subsurface including the steps of:
(i) contacting the dental surface with a protein disrupting agent, and
(ii) contacting the dental surface with a composition of the invention.

The dental surface is preferably dental enamel. In one embodiment the dental surface is a lesion in the enamel, such as a lesion caused by caries, dental erosion or fluorosis. Any suitable protein disrupting agent can be used in the method of the present invention. The agent is required to reduce the proteinaceous barrier formed over the surface to be treated, such as the pellicle over teeth. Examples of suitable agents include bleach, detergent, chaotropic agents such as urea, high phosphate concentrations, cocktails of proteases (e.g. endopeptidases, proteinases and exopeptidases) and any other protein solubilizing, disrupting or hydrolysing agent. Examples of suitable bleaches include sodium hypochlorite (NaOCl), and cabamide peroxide bleaches. In a preferred embodiment, the bleach is an alkaline bleach. In a further preferred embodiment the alkaline bleach is NaOCl. The protein disrupting agent acts to solubilize and partially or wholly remove proteins from the dental surface, particularly proteins of the pellicle.

A composition as described herein may further include free fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

The fluoride ions are preferably present in the composition in an amount greater than 1 ppm. More preferably, the amount is more than 3 ppm. In another embodiment, it is preferably more than 10 ppm. In typical embodiments described below, the amount may be several hundred or thousand ppm. The fluoride content is typically measured as a ppm in oral compositions in the manner commonly used in the art. Where the fluoride is provided from a source with the stabilized ACP, the ppm refers to the concentration of the fluoride in that source, typically a solution or suspension of bioavailable fluoride.

In any aspect or embodiments as described herein, the stabilized ACP and/or ACFP is phosphopeptide (PP)-stabilized. Preferably, the phosphopeptide (as defined below) is a casein phosphopeptide. Preferably, the ACP or ACFP is in the form of a casein phosphopeptide stabilized ACP or ACFP complex.

"Phosphopeptide" in the context of the description of this invention means an amino acid sequence in which at least one amino acid is phosphorylated. Preferably, the phosphopeptide includes one or more of the amino acid sequence -A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys. Preferably at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

In one embodiment, the ACP or ACFP is stabilized by a casein phosphopeptide (CPP), which is in the form of intact casein or fragment of the casein, and the complex formed preferably has the formula $[CPP(ACP)_8]_n$ or $[(CPP)(ACFP)_8]_n$, where n is equal to or greater than 1, for example 6. The complex formed may be a colloidal complex, where the core particles aggregate to form large (eg 100 nm) colloidal particles suspended in water. Thus, the PP can be a casein protein or a phosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence -A-B-C- or A-B-C-D-E as described above. The sequence flanking this core sequence may be any sequence. However, those flanking sequences in $\alpha_{s1}(59\ 79)$, $\beta(1-25)$, $\alpha_{s2}(46-70)$ and $\alpha_{s2}(1-21)$ are preferred. The flanking sequences may optionally be modified by deletion, addition or conservative substitution of one or more residues. The amino acid composition and sequence of the flanking region are not critical.

The phosphopeptide may be selected from any described in WO2006/056013, WO2006/135982 or U.S. Pat. No. 5,015,628.

Examples of conservative substitutions are shown in Table 1 below.

TABLE 1

| Original Residue | Exemplary Conservative Substitution | Preferred Conservative Substitution |
| --- | --- | --- |
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Glu | Glu |
| Thr | Ser | Ser |
| Trp | Tyr | Tyr |
| Tyr | Trp Phe Thr Ser | Phe |

The flanking sequences may also include non-naturally occurring amino acid residues.

Commonly encountered amino acids which are not encoded by the genetic code, include:

2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2, 3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (AIle) for Ile, Leu, and Val;
ρ-amidinophenylalanine for Ala;
N-methylglycine (MeGly, sarcosine) for Gly, Pro, Ala.
N-methylisoleucine (MeIle) for Ile;
Norvaline (Nva) for Met and other aliphatic amino acids;
Norleucine (Nle) for Met and other aliphatic amino acids;
Ornithine (Orn) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I) phenylalanine, triflourylphenylalanine, for Phe.

In one embodiment, the PP is one or more phosphopeptides selected from the group consisting of $\alpha_{s1}(59\ 79)$, $\beta(1-25)$, $\alpha_{s2}(46-70)$ and $\alpha_{s2}(1-21)$.

In another embodiment of the invention, the stabilized ACFP or ACP complex and a compound capable of increasing or maintaining the pH of a solution is incorporated into oral compositions such as toothpaste, mouth washes or formulations for the mouth to aid in the prevention and/or treatment of dental caries, tooth decay, dental erosion or fluorosis. The ACFP or ACP complex may comprise 0.01-50% by weight of the composition, preferably 1.0-50%. For oral compositions, it is preferred that the amount of the CPP-ACP and/or CPP-ACFP administered is 0.01-50% by weight, preferably 1.0%-50% by weight of the composition. In a particularly preferred embodiment, the oral composition of the present invention contains about 2% CPP-ACP, CPP-ACFP or a mixture of both. The oral composition of this invention which contains the above-mentioned agents may be prepared and used in various forms applicable to the mouth such as dentifrice including toothpastes, toothpowders and liquid dentifrices, mouthwashes, mouthrinses, mouth sprays, varnish, dental cement, troches, chewing gums, dental pastes, gingival massage creams, gargle tablets, dairy products and other foodstuffs. The oral composition according to this invention may further include additional well known ingredients depending on the type and form of a particular oral composition.

In certain preferred forms of the invention the oral composition may be substantially liquid in character, such as a mouthwash, rinse or spray. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

In other desirable forms of this invention, the composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 $cm^2/g$., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a jar of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like. The composition of the invention may be a dual phase composition wherein each phase permits release of components over different time periods. For example, in use a dual phase composition may release stabilized ACP and/or ACFP, preferably CPP-ACP and/or CPP-ACFP, from a first phase at a faster rate than a compound that is capable of increasing or maintaining the pH of a solution from a second phase. Preferably, the dual phase composition is a dual phase chewing gum.

In a further aspect, the invention provides compositions including pharmaceutical compositions comprising any of the ACFP and/or ACP complexes as described above together with a compound capable of increasing or maintaining the pH of a solution and a pharmaceutically-acceptable carrier. Such compositions may be selected from the group consisting of dental, anticariogenic compositions and therapeutic compositions. Dental compositions or therapeutic compositions may be in the form of a gel, liquid, solid, powder, cream or lozenge. Therapeutic compositions may also be in the form of tablets or capsules. In one embodiment, the ACP and/or ACFP complexes are substantially the only remineralizing active components of such a composition. For example, a crème formulation may be employed containing: water; glycerol; CPP-ACP; D-sorbitol; silicon dioxide; sodium carboxymethylcellulose (CMC-Na); propylene glycol; titanium dioxide; xylitol; phosphoric acid; guar gum; zinc oxide; sodium saccharin; ethyl p-hydroxybenzoate; magnesium oxide; butyl p hydroxybenzoate and propyl p-hydroxybenzoate.

The invention further includes a formulation described above provided together with instructions for its use to treat or prevent any one or more of dental caries or tooth decay, dental erosion and fluorosis.

In one embodiment, the active components of the composition consist essentially of the compound capable of increasing or maintaining the pH of a solution and stabilized ACP and/or ACFP. It is believed, without being bound by any theory or mode of action, that the stabilized ACP and/or ACFP and the compound capable of increasing or maintaining the pH of a solution are central to the therapeutic or preventative effect of the above embodiments of the invention, and thus embodiments consisting essentially of those components (with carriers, excipients and the like as required) are included within the scope of the invention.

The invention also relates to a kit for the treatment or prevention of one or more of dental caries, fluorosis and dental erosion including (a) a compound capable of increasing or maintaining the pH of a solution and (b) a CPP-ACP or CPP-ACFP complex in a pharmaceutically acceptable carrier. Desirably, the kit further includes instructions for their use for the mineralization of a dental surface in a patient in need of such treatment. The instructions may describe the use of the kit to treat or prevent one or more of each of dental caries, tooth decay, dental erosion and fluorosis. In one embodiment, the agent and the complex are present in suitable amounts for treatment of a patient. The instructions may direct the user to apply the a compound capable of increasing or maintaining the pH of a solution before, simultaneously or after a CPP-ACP or CPP-ACFP complex in a pharmaceutically acceptable carrier.

In another aspect a kit of the invention is constructed so that a compound capable of increasing or maintaining the pH of a solution is dispensed simultaneously or after a CPP-ACP or CPP-ACFP complex in a pharmaceutically acceptable carrier.

In a further aspect, there is provided a method of treating or preventing one or more of each of dental caries, tooth decay, dental erosion and fluorosis, comprising the steps of administering a compound capable of increasing or maintaining the pH of a solution to the teeth of a subject followed by administering an ACP or ACFP complex or composition. Topical administration of the complex is preferred. The method preferably includes the administration of the complex in a formulation as described above.

In a further aspect there is provided the use of a compound capable of increasing or maintaining the pH of a solution and a stabilized amorphous calcium phosphate (ACP) or amorphous calcium fluoride phosphate (ACFP) in a manufacture of a composition for the treatment and/or prevention of one or more of dental caries, tooth decay, dental erosion and fluorosis.

In a further aspect there is provided a composition comprising as an active agent a compound capable of increasing or maintaining the pH of a solution and a stabilized amorphous calcium phosphate (ACP) or amorphous calcium fluoride phosphate (ACFP) for mineralizing a dental surface or subsurface. Typically, mineralizing a dental surface or subsurface is for the treatment and/or prevention of one or more of dental caries, tooth decay, dental erosion and fluorosis.

According to a further aspect of the invention there is provided a composition for dental restoration, including a dental restorative material to which has been added a composition of the invention. The base of the dental restorative material can be a glass ionomer cement, a composite material or any other restorative material which is compatible. It is preferred that the amount of stabilized ACP or ACFP, preferably CPP-ACP complex or CPP-ACFP complex, included in the dental restorative material is 0.01-80% by weight, preferably 0.5 10% and more preferably 1-5% by weight. The dental restorative material of this invention which contains the above mentioned agents may be prepared and used in various forms applicable to dental practice. The dental restorative material according to this embodiment may further include other ions, eg. antibacterial ions $Zn^{2+}$, $Ag^+$, etc or other additional ingredients depending on the type and form of a particular dental restorative material. It is preferable that the pH of dental restorative material according to this embodiment be between 2-10, more preferably 5-9 and even more preferably 5-7. It is preferable that the pH of the dental restorative material containing the CPP-ACP complex or ACFP complex be in the range of about 2 to 10, more preferably in the range of about 5 to 9 and even more preferably in the range of about 5 to 7.

According to a further aspect of the invention there is provided a varnish including a compound that is capable of increasing or maintaining the pH of a solution and a mineralizing agent. Preferably, the mineralizing agent is any stabilized ACP and/or ACFP complex as described herein.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

The invention will now be further described with reference to the following non-limiting examples.

One example of a mineralizing composition or agent comprises the following (in decreasing order of proportion):
water
glycerol
CPP-ACP
D-sorbitol
silicon dioxide
sodium carboxymethylcellulose (CMC-Na)
propylene glycol
titanium dioxide
xylitol
phosphoric acid
guar gum
zinc oxide sodium saccharin
ethyl p-hydroxybenzoate
magnesium oxide
butyl p-hydroxybenzoate
propyl p-hydroxybenzoate Such a composition is available from GC corporation under the name Tooth Mousse™. This is suitable for use after a compound capable of increasing or maintaining the pH of a solution and is in the form of a paste or crème to facilitate its retention on teeth for a suitable period. Alternatively, this mineralizing composition may contain a compound capable of increasing or maintaining the pH of a solution.

Example 1

Preparation of CPP-ACFP and CPP-ACP Solutions

Stock solutions of 3.25M $CaCl_2$), 1.25 M $Na_2HPO_4$, 1 M NaOH and 1M NaF were added in approximately thirty aliquots to a 10-15% w/v tryptic digest of casein until a final concentration of approximately 78 mM $Ca^{2+}$, 48 mM phosphate and 12 mM fluoride concentrations were obtained. The solutions were added slowly (that is, less than approximately 1% volume addition per minute). An aliquot of the phosphate solution was added first, followed by an aliquot of the calcium solution. The pH was maintained at 7.0, 6.5, 6.0, 5.5 and 5.0 using the NaOH with thorough mixing. The sodium hydroxide solution was added automatically by a pH stat with the addition of the hydroxide ions usually being after each addition of the calcium ions. After addition of the calcium ions, phosphate ions, hydroxide ions and fluoride ions the solution was filtered through a 0.1 micron filter to concentrate 1-2 fold. The retentate may be washed with water to remove salts and inactive (and bitter tasting) peptides if desired. CPP-ACP solutions were prepared as above without the addition of fluoride.

Example 2

Determining Loosely and Tightly Bound Calcium and Phosphate

At the completion of the titration and filtration for each pH in Example 1, a sample of each retentate was taken and less than 10% collected as a filtrate using a 3000 molecular weight cut-off Centriprep 3 ultrafiltration membrane. The Centripreps containing the samples were centrifuged at 1,000 g for 15 min in a Beckman J2-21 centrifuge using a JA 10.5 rotor. The original sample before Centriprep centrifugation and a sample of the filtrate after Centriprep centrifugation were taken for analysis of calcium, phosphate and fluoride concentrations. The analysis of the original sample gave total calcium, phosphate and fluoride ion concentrations and the analysis of the filtrate gave loosely bound calcium, phosphate and fluoride concentrations. The difference between the total and loosely bound concentrations is the tightly bound concentration of Ca, Pi and F by the CPP.

Example 3

Preparation of CPP-ACFP and CPP-ACP Solutions

Recaldent® (CPP-ACP) was purchased from Recaldent Pty Ltd, Victoria, Australia. The product (#841117) contained 14.3% calcium, 22.3% phosphate and 47% casein phosphopeptide on a weight basis. The product was dissolved at 0.5% and adjusted to pH 5.5 by the addition of HCl. Calcium and phosphate ions were then added by titrating 3.25 M $CaCl_2$) and 2M $NaH_2PO_4$ while keeping the pH at 5.5 with the addition of 2.5 M NaOH. The titration of calcium and phosphate ions was continued until the solution became translucent. The concentration of calcium and phosphate added was recorded.

The solution may also be formed by titrating calcium and phosphate ions into a 0.5% CPP-ACP solution and letting the pH fall to 5.5 by the addition of further calcium phosphate.

TABLE 2

| Calcium and phosphate levels of normal and superloaded CPP-ACP | | | | |
|---|---|---|---|---|
| | Calcium | | Phosphate | |
| | mmol/L | mol/mol CPP | mmol/L | mol/mol CPP |
| Normal 0.5% w/v CPP-ACP | 17.8 | 22.8 | 11.6 | 14.8 |
| Superloaded 0.5 w/v CPP-ACP (sCPP-ACP) | 37.8 | 48.3 | 23.6 | 30.2 |

These results demonstrate that CPP-ACP can be superloaded with calcium and phosphate ions to produce thermodynamically stable complexes in a metastable solution.

Example 4

Preparation of a Formulation of CPP-ACP and Calcium Phosphate

In another example Recaldent® (CPP-ACP) powder was dry blended with $CaHPO_4$ powder in the ratio CPP-ACP:$CaHPO_4$ equals 1:10 on a weight basis. This powder was then added to sugar-free gum and toothpaste formulations at 1-5% w/w.

Example 5

A topical crème may be produced in accordance with the present invention having the following ingredients:
Water
glycerol
Stabilized ACP and/or ACFP
A compound capable of increasing or maintaining the pH of a solution
D-sorbitol
sodium carboxymethylcellulose (CMC-Na)
propylene glycol
silicon dioxide
titanium dioxide
xylitol
phosphoric acid
sodium fluoride
flavouring
sodium saccharin
ethyl p-hydroxybenzoate
propyl p-hydroxybezoate
butyl p-hydroxybenzoate

Example 6

A mouthrinse formulation be produced in accordance with the present invention having the following composition:

Water
Alcohol
Poloxamer 407
Sodium Lauryl Sulphate
Stabilized ACP and/or ACFP
A compound capable of increasing or maintaining the pH of a solution
Sodium Fluoride
Flavours
Sodium Saccharin
Ethyl p-hydroxybenzoate
Propyl p-hydroxybenzoate
Butyl p-hydroxybenzoate Example 7

A sugar-free chewing gum formulation be produced in accordance with the present invention having the following composition:
Crystalline sorbitol/mannitol/xylitol
Gum base
Calcium carbonate
Glycerine
Stabilized ACP and/or ACFP
A compound capable of increasing or maintaining the pH of a solution
Sodium Fluoride
Flavour oil
Water Example 8

The effectiveness of the invention could be demonstrated by the experiments described below. Seven premolar teeth with FLE (Thylstrup Fejerskov Index, TF=3) could be selected from teeth extracted for orthodontic reasons from healthy patients aged 10-28 years from the Royal Dental Hospital of Melbourne, Australia. Informed patient consent should be obtained for the extracted teeth and the study protocol approved by the Human Research Ethics Committee of The University of Melbourne. All specimens should then be debrided of adherent soft tissue and stored in 18% w/v formalin acetate solution at room temperature.

The teeth are then cleaned with a rotating rubber cup and pumice and rinsed in double de-ionized water (DDW) (Fejerskov et al., 1988). The anatomical crowns are sectioned from the roots using a water-cooled diamond blade. Each crown is sectioned to provide a pair of enamel blocks each containing a FLE. A 4×4 mm$^2$ window should be created over each lesion by placing a rectangular piece of Parafilm® (American National Can, Chicago, Ill., USA.) over the lesion and covering the surrounding enamel with nail varnish (Revlon™, New York, USA). The parafilm would then be carefully removed to reveal the enamel lesion window which was divided into halves as control and test windows. The control window was covered with nail varnish. The two lesions of each specimen should be randomly assigned to one of two remineralization groups; Group I—treatment with 5% w/v CPP-ACFP or CPP-ACP and Group II—treatment with 5% w/v CPP-ACFP or CPP-ACP immediately following pre-conditioning with a compound that is capable of increasing or maintaining the pH of a solution. Group II could alternatively be simultaneous addition of CPP-ACFP or CPP-ACP with a compound that is capable of increasing or maintaining the pH of a solution. Alternatively, Group II could be addition of CPP-ACP or CPP-ACFP followed by a compound that is capable of increasing or maintaining the pH of a solution.

CPP-ACFP is obtained from Recaldent Pty Ltd (Melbourne, Australia) and contains 47.6% w/w CPP, 15.7% w/w $Ca^{2+}$, 22.9% w/w $PO_4^{3-}$ and 1.2% w/w F—. The CPP-ACFP is dissolved in distilled and deionized water at 5% w/v and adjusted to pH 7.0 with HCl. For the first group, each specimen should be placed in 2 ml of 5% w/v, CPP-ACFP in a 5 ml plastic vial at 37° C. The CPP-ACFP solution should be changed daily for 10 days. For the second group, each specimen should be placed in solution containing a compound that is capable of increasing or maintaining the pH of a solution for 20 mins, rinsed and then placed in 2 ml of 5% w/v CPP-ACFP in a 5 ml plastic vial at 37° C. The CPP-ACFP solution may be changed daily for 10 days.

A Chroma Meter (Minolta ChromaMeter CR241, Minolta, Japan) is used to record surface reflectance. Surface reflectance measurement is established in L*a*b* color space by the Commission de L'Eclairage in 1978, and measurements relate to human colour perception in three colour dimensions (Commision Internationale de L'Eclaige, 1978). The L* values represent colour gradients from white to black, a* values represent colour gradients from green to red, and b* values represent colour gradients from blue to yellow (Commision Internationale de L'Eclaige, 1978). Only L* value measurements can be used with whiter colours having a higher reading, and darker colours a lower reading. To ensure a reproducible position of specimens in the Chroma Meter, a wax mold for each sample can be prepared and stored. All samples were air-dried with a dental triplex syringe for 60 s before each measurement. Individual specimens can be repositioned ten times both before and after treatment, and colour reflectance L* values were recorded.

Each specimen is removed from the mineralizing solution and rinsed in DDW for 60 s and blotted dry with blotting paper. The nail varnish on the control window is removed gently with acetone. The control and test windows are then separated by cutting through the midline between the windows. The two half-slabs should then placed with the lesion windows parallel and embedded in cold curing methacrylate resin (Paladur, Heraus Kulzer, Germany). The two paired enamel half-slabs are sectioned, and subjected to microradiography and microdensitometric image analysis to determine mineral content exactly as described by Shen et al. (2001).

An area free of defects close to the midline of each microradiographic image of each lesion (control and test) can be chosen and scanned six times (Shen et al., 2001). Each scan comprised 200 readings, taken from the enamel surface to the mid-enamel region to include the total fluorotic lesion. The test (CPP-ACFP-treated) lesion should be scanned to exactly the same depth as the control (untreated) lesion. The gray values obtained from each scan are converted to the equivalent thickness of aluminium (tA) using the image of the aluminium stepwedge included with each section (Shen et al., 2001). Using the formula of Angmar et al. (1963), the percentage volume of mineral was obtained for each reading as follows: V=(52.77(tA)−4.54)/tS. Where: V=volume of mineral as a percentage; tA=the relative thickness of aluminium obtained from the gray value scanned; and tS=section thickness (80 μm).

From the densitometric profile of [(vol % min versus lesion depth (mm)] for each lesion DZ values were calculated using trapezoidal integration (Reynolds, 1997). The difference between the area under the profile of the untreated fluorotic enamel in the control window with adjacent normal enamel is designated DZf, and the difference between the area under the CPP-ACFP-treated fluorotic enamel in the test window and adjacent normal enamel is designated DZr. Percentage mineralization (% M) of the fluorotic lesion was therefore (1−DZr/(DZf)×100 (Reynolds, 1997).

Following the microradiography the sections containing both control and mineralized FLE can be subjected to Energy Dispersive X-ray Analysis (EDAX) as described previously (Reynolds, 1997). Mean L* values can be compared using a one way classification analysis of variance (ANOVA) with a Scheffe multiple comparison. The mean % M values can also be compared using a one-way ANOVA. Overall mean L* and % M values are analysed using a paired data Student's t-test.

Example 9

The Effect of Hypochlorite on Enamel Subsurface Remineralization by CPP-ACP

Human tooth enamel demineralized subsurface lesions were prepared using the method of Reynolds, (1997). J Dent Res 76:1587-1595. The enamel surface was removed by polishing to remove all adsorbed protein. This removed around 50-100 μm of enamel to expose an uncoated, polished enamel surface for the study. Furthermore, the acid buffer used to produce the subsurface lesions did not contain protein such that no protein would have entered these subsurface lesions. A 1% w/v CPP-ACP pH 5.0 solution was prepared using Recaldent® [Kraft Foods], a commercial source of CPP-ACP that is prepared as per Example 1 at a pH of 5.0. All blocks were remineralized with the 1% CPP-ACP pH 5 solution for 7 days at 37° C. However, half were exposed to a 1% v/v sodium hypochlorite solution for 1 min at the start of the CPP-ACP remineralization period. In other words, the sodium hypochlorite and CPP-ACP were simultaneously exposed to the subsurface lesion. After remineralization the enamel blocks were embedded, sectioned and subjected to transverse microradiography and densitometric image analysis as previously described by Reynolds (1997) to determine percent mineral content gain (% Remineralization) shown in Table 3. A one way analysis of variance with differences in means determined using a Tukey HSD post hoc comparison showed that the treatment with hypochlorite significantly increased the level of remineralization by the CPP-ACP solution by 31%.

Without being bound by any theory or mode of action it is believed that the mechanism of enhanced CPP-ACP remineralization by the hypochlorite is related to the diffusion of the hypochlorite into the enamel subsurface lesions. Once in the lesion fluid it slowly decomposed, thereby releasing chlorine, oxygen, sodium and hydroxide ions.

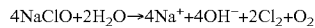

$$4NaClO + 2H_2O \rightarrow 4Na^+ + 4OH^- + 2Cl_2 + O_2$$

This slow breakdown of the hypochlorite in the enamel subsurface lesion produced base (hydroxide ions) which increased the degree of saturation of hydroxyapatite in the intra-lesion fluid as a result of the additional hydroxide ions. It is believed that the formation of hydroxyapatite is inhibited by protons which may be released as ACP coverts to hydroxyapatite or which are present in lower pH environments such as during caries formation. In these ways, the additional hydroxide ions, or pH maintained at or above neutral, facilitates the formation of hydroxyapatite (mineralization) by the CPP-ACP in the lesion. Hence hypochlorite is a non-limiting example of an intra-lesion base producing compound that will drive remineralization by CPP-ACP or CPP-ACFP.

TABLE 3

Remineralization of Enamel Subsurface lesions by 1% w/v CPP-ACP with and without 1% v/v Hypochlorite treatment

| Treatment | Lesion Depth | ΔZd | ΔZr | ΔZd-ΔZr | % Remin. |
|---|---|---|---|---|---|
| 1% CPP-ACP | 109.16 ± 11.89 | 3316.59 ± 601.49 | 2153.24 ± 417.85$^c$ | 1163.35 ± 352.97 | 34.82 ± 6.88 |
| 1% CPP-ACP and 1% Hypochlorite | 106.65 ± 16.80 | 2986.46 ± 725.39 | 1629.30 ± 446.94 | 1357.16 ± 365.43 | 45.48 ± 5.49 |
| p-value | | | | | p < 0.001 |

It will be understood that the invention disclosed and defined in this specification extends to all alternative combinations of two or more of the individual features mentioned or evident from the text or figures or tables. All of these different combinations constitute various alternative aspects of the invention.

REFERENCES

Fejerskov O, Baelum V, Manji F, Moller 1 (1988). Dental Fluorosis—A handbook for health workers Copenhagen: Munksgard.

Reynolds E C (1998). Anticariogenic complexes of amorphous calcium phosphate stabilized by casein phosphopeptides: a review. Spec Care Dentist 18:8-16.

Reynolds E C, Cai F, Shen P, Walker G D (2003). Retention in plaque and remineralization of enamel lesions by various forms of calcium in a mouthrinse or sugar-free chewing gum. J Dent Res 82:206-11.

Shen P, Cai F, Nowicki A, Vincent J, Reynolds E C (2001). Remineralization of enamel subsurface lesions by sugar-free chewing gum containing casein phosphopeptide-amorphous calcium phosphate. J Dent Res 80:2066-70.

The invention claimed is:

1. A method of reducing tooth sensitivity in a patient in need thereof, comprising
    (i) contacting a tooth with a first composition comprising stabilized amorphous calcium phosphate (ACP) and/or stabilized amorphous calcium fluoride phosphate (ACFP), and
    (ii) subsequently to (i) and within 1 to 60 minutes of (i), contacting the tooth with a second composition comprising a base, thereby reducing tooth sensitivity in the patient.

2. The method of claim 1, wherein the stabilized ACP and/or the stabilized ACFP are contacted with the tooth for a period of time selected from about 1 minute to 2 hours, about 5 minutes to 60 minutes, and about 10 minutes.

3. The method of claim 1, wherein the second composition is contacted with the tooth for a period of time selected from about 1 to 60 minutes, about 1 to 30 minutes, and about 20 minutes.

4. The method of claim 1, wherein the stabilized ACP and/or the stabilized ACFP is repeatedly applied to the tooth.

5. The method of claim 4, wherein the stabilized ACP and/or the stabilized ACFP is repeatedly applied to the tooth over a period of 1 day to several months.

6. The method according to claim 1, wherein the stabilized ACP and/or the stabilized ACFP is in a form selected from toothpaste, toothpowder, liquid dentifrice, mouthwash, mouthrinse, mouth spray, varnish, dental cement, troche, chewing gum, lozenge, dental paste, gingival massage cream, gargle tablet, dairy product, and other foodstuffs.

7. The method according to claim 1, wherein the second composition is capable of maintaining the pH of a solution between 7 to 9.

8. The method according to claim 1, wherein the second composition is capable of maintaining the pH of a solution at about 7.5.

9. The method according to claim 1, wherein the second composition is provided in an amount effective to raise the pH of intra-lesion fluid of a dental lesion from 6 to 7.5.

10. The method according to claim 1, wherein the base is selected from sodium bicarbonate, sodium hypochlorite, and urea.

11. The method according to claim 7, wherein the second composition is a mouthrinse comprising sodium bicarbonate or a mouthwash comprising sodium bicarbonate.

12. The method according to claim 1, wherein the contacting of step (ii) is effected 1 to 30 minutes after the contacting of step (i).

13. The method according to claim 1, wherein the contacting of step (ii) is effected 1 to 5 minutes after the contacting of step (i).

14. The method according to claim 1, wherein the stabilized ACP is casein phosphopeptide stabilized amorphous calcium phosphate (CPP-ACP).

15. The method according to claim 1, wherein the stabilized ACFP is casein phosphopeptide stabilized amorphous calcium fluoride phosphate (CPP-ACFP).

16. The method according to claim 1, wherein the stabilized ACP is casein phosphopeptide stabilized amorphous calcium phosphate (CPP-ACP) and the stabilized ACFP is casein phosphopeptide stabilized amorphous calcium fluoride phosphate (CPP-ACFP).

17. The method according to claim 1, wherein the base is sodium hydroxide.

* * * * *